(12) United States Patent
Fulkerson et al.

(10) Patent No.: US 10,987,460 B2
(45) Date of Patent: Apr. 27, 2021

(54) METHODS AND SYSTEMS OF GENERATING RAPIDLY VARYING PRESSURE AMPLITUDES IN FLUIDIC CIRCUITS IN A DIALYSIS TREATMENT SYSTEM

(71) Applicant: Fresenius Medical Care Holdings, Inc., Waltham, MA (US)

(72) Inventors: Barry Neil Fulkerson, Longmont, CO (US); Nhan Viet Pham, Fountain Valley, CA (US); Alec Huang, Irvine, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 945 days.

(21) Appl. No.: 15/453,620

(22) Filed: Mar. 8, 2017

(65) Prior Publication Data

US 2017/0258979 A1    Sep. 14, 2017

Related U.S. Application Data

(60) Provisional application No. 62/305,206, filed on Mar. 8, 2016.

(51) Int. Cl.
| | | |
|---|---|---|
| *A61M 1/34* | (2006.01) | |
| *F04B 43/00* | (2006.01) | |
| *A61M 1/10* | (2006.01) | |
| *F04B 43/12* | (2006.01) | |
| *A61M 1/36* | (2006.01) | |

(52) U.S. Cl.
CPC ........ *A61M 1/3403* (2014.02); *A61M 1/1039* (2014.02); *A61M 1/1086* (2013.01); *A61M 1/341* (2014.02); *A61M 1/3455* (2013.01); *F04B 43/0072* (2013.01); *F04B 43/0081* (2013.01);
(Continued)

(58) Field of Classification Search
CPC .............. A61M 1/3403; A61M 1/1605; A61M 1/1039; A61M 1/3451; A61M 1/1086; A61M 1/3455; A61M 1/3672; F04B 43/0081; F04B 43/1253
See application file for complete search history.

(56) References Cited

U.S. PATENT DOCUMENTS

| 3,242,456 A | 3/1966 | Duncan |
| 3,803,913 A | 4/1974 | Tracer |

(Continued)

FOREIGN PATENT DOCUMENTS

| CN | 101291704 A | 10/2008 |
| CN | 102089020 A | 6/2011 |

(Continued)

OTHER PUBLICATIONS

International Search Report for PCT/US17/21389, dated Jun. 15, 2017.

(Continued)

*Primary Examiner* — Philip R Wiest
(74) *Attorney, Agent, or Firm* — Novel IP

(57) ABSTRACT

The present specification describes a modular, portable hemofiltration system, for providing improved clearance levels of blood toxins, which includes at least one roller pump that is designed and operated to generate a rapidly varying pressure profile of fluid within at least a blood circuit of the hemofiltration system.

40 Claims, 12 Drawing Sheets

(52) U.S. Cl.
CPC ....... *F04B 43/1253* (2013.01); *A61M 1/3672* (2013.01)

(56) References Cited

U.S. PATENT DOCUMENTS

| | | | |
|---|---|---|---|
| 3,961,918 A | 6/1976 | Johnson |
| 3,989,625 A | 11/1976 | Mason |
| 4,354,562 A | 10/1982 | Newman |
| 4,397,519 A | 8/1983 | Cooney |
| 4,403,765 A | 9/1983 | Fisher |
| 4,430,098 A | 2/1984 | Bowman |
| 4,480,483 A | 11/1984 | McShane |
| 4,531,799 A | 7/1985 | Gray |
| 4,535,637 A | 8/1985 | Feller |
| 4,586,576 A | 5/1986 | Inoue |
| 4,740,755 A | 4/1988 | Ogawa |
| 4,828,543 A | 5/1989 | Weiss |
| 5,000,274 A | 3/1991 | Bullivant |
| 5,074,368 A | 12/1991 | Bullivant |
| 5,114,580 A | 5/1992 | Ahmad |
| 5,170,789 A | 12/1992 | Narayan |
| 5,228,308 A | 7/1993 | Day |
| 5,258,127 A | 11/1993 | Gsell |
| 5,725,776 A | 3/1998 | Kenley |
| 5,782,796 A | 7/1998 | Din |
| 5,915,932 A * | 6/1999 | Nabity .................. E21B 43/121 417/477.1 |
| 5,954,971 A | 9/1999 | Pages |
| 5,989,438 A | 11/1999 | Fumiyama |
| 6,044,691 A | 4/2000 | Kenley |
| 6,358,225 B1 | 3/2002 | Butterfield |
| 6,487,904 B1 | 12/2002 | Myhre |
| 6,491,656 B1 | 12/2002 | Morris |
| 6,638,478 B1 | 10/2003 | Treu |
| 6,653,841 B1 | 11/2003 | Koerdt |
| 6,681,624 B2 | 1/2004 | Furuki |
| 6,691,047 B1 | 2/2004 | Fredericks |
| 6,752,172 B2 | 6/2004 | Lauer |
| 6,836,201 B1 | 12/2004 | Devenyi |
| 6,948,697 B2 | 9/2005 | Herbert |
| 7,087,026 B2 | 8/2006 | Callister |
| 7,097,148 B2 | 8/2006 | DeWall |
| 7,270,015 B1 | 9/2007 | Feller |
| 7,387,022 B1 | 6/2008 | Korniyenko |
| 8,040,493 B2 | 10/2011 | Fulkerson |
| 8,105,487 B2 | 1/2012 | Fulkerson |
| 8,114,288 B2 | 2/2012 | Robinson |
| 8,137,553 B2 | 3/2012 | Fulkerson |
| 8,240,636 B2 | 8/2012 | Smith |
| 8,395,761 B2 | 3/2013 | Fulkerson |
| 8,475,399 B2 | 7/2013 | Fulkerson |
| 8,535,522 B2 | 9/2013 | Fulkerson |
| 8,597,505 B2 | 12/2013 | Fulkerson |
| 8,771,511 B2 | 7/2014 | Robinson |
| 9,157,786 B2 | 10/2015 | Fulkerson |
| 9,199,022 B2 | 12/2015 | Fulkerson |
| 9,201,036 B2 | 12/2015 | Fulkerson |
| 9,295,772 B2 | 3/2016 | Fulkerson |
| 9,308,307 B2 | 4/2016 | Fulkerson |
| 9,352,282 B2 | 5/2016 | Fulkerson |
| 9,354,640 B2 | 5/2016 | Byler |
| 9,358,331 B2 | 6/2016 | Fulkerson |
| 9,360,129 B2 | 6/2016 | Smith |
| 9,415,152 B2 | 8/2016 | Robinson |
| 9,517,296 B2 | 12/2016 | Fulkerson |
| 9,759,710 B2 | 9/2017 | Fulkerson |
| 2002/0151804 A1 | 10/2002 | O'Mahony |
| 2002/0158019 A1 | 10/2002 | Collins |
| 2003/0048185 A1 | 3/2003 | Citrenbaum |
| 2003/0056585 A1 | 3/2003 | Furuki |
| 2003/0220598 A1 | 11/2003 | Busby |
| 2004/0031756 A1 | 2/2004 | Suzuki |
| 2005/0086008 A1 | 4/2005 | DiGianfilippo |
| 2005/0101901 A1 | 5/2005 | Gura |
| 2005/0131332 A1 | 6/2005 | Kelly |
| 2005/0133439 A1 | 6/2005 | Blickhan |
| 2006/0195064 A1 | 8/2006 | Plahey |
| 2006/0226057 A1 | 10/2006 | Robinson |
| 2006/0289342 A1 | 12/2006 | Sugioka |
| 2007/0112297 A1 | 5/2007 | Plahey |
| 2007/0179425 A1 | 8/2007 | Gura |
| 2007/0253463 A1 | 11/2007 | Perry |
| 2007/0269340 A1 | 11/2007 | Dannenmaier |
| 2008/0041792 A1 | 2/2008 | Crnkovich |
| 2008/0214979 A1 | 9/2008 | Brugger |
| 2008/0230450 A1 | 9/2008 | Burbank |
| 2008/0258735 A1 | 10/2008 | Quackenbush |
| 2008/0290974 A1 | 11/2008 | Adams |
| 2009/0008306 A1 | 1/2009 | Cicchello |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0127193 A1 | 5/2009 | Updyke |
| 2010/0129247 A1 | 5/2010 | Lauer |
| 2010/0140149 A1 | 6/2010 | Fulkerson |
| 2010/0331754 A1 | 12/2010 | Fulkerson |
| 2011/0054378 A1 | 3/2011 | Fulkerson |
| 2011/0071465 A1 | 3/2011 | Wang |
| 2011/0142700 A1 * | 6/2011 | Gura .................. A61M 1/1696 417/474 |
| 2011/0303598 A1 | 12/2011 | Lo |
| 2011/0315611 A1 | 12/2011 | Fulkerson |
| 2012/0214117 A1 | 8/2012 | Broker |
| 2013/0220907 A1 | 8/2013 | Fulkerson |
| 2013/0280104 A1 | 10/2013 | Heide |
| 2014/0188040 A1 * | 7/2014 | Busby .................. A61M 1/28 604/29 |
| 2014/0276537 A1 | 9/2014 | Kruse |
| 2015/0258263 A1 * | 9/2015 | Hogard .............. A61M 1/1605 210/103 |
| 2015/0314055 A1 | 11/2015 | Hogard |
| 2016/0069732 A1 | 3/2016 | Fulkerson |
| 2016/0109398 A1 | 4/2016 | Fulkerson |
| 2016/0317733 A1 | 11/2016 | Fulkerson |
| 2016/0319954 A1 | 11/2016 | Smith |
| 2017/0007756 A1 | 1/2017 | Robinson |
| 2017/0021085 A1 | 1/2017 | Fulkerson |
| 2017/0021088 A1 | 1/2017 | Fulkerson |
| 2017/0021306 A1 | 1/2017 | Fulkerson |
| 2017/0023953 A1 | 1/2017 | Byler |
| 2017/0232177 A1 | 8/2017 | Fulkerson |

FOREIGN PATENT DOCUMENTS

| | | |
|---|---|---|
| CN | 102427835 A | 4/2012 |
| JP | 2002139165 A | 5/2002 |
| WO | 20015069412 A1 | 7/2001 |
| WO | 2009073567 | 6/2009 |
| WO | 2010042666 | 4/2010 |
| WO | 2010062698 | 6/2010 |
| WO | 2010081121 | 7/2010 |
| WO | 2012108910 | 8/2012 |
| WO | 2014105267 A1 | 7/2014 |
| WO | 2014105755 | 7/2014 |
| WO | 2014161008 | 10/2014 |
| WO | 2017106356 A1 | 6/2017 |

OTHER PUBLICATIONS

International Search Report for PCT/US13/77234, dated Jun. 9, 2014.

International Search Report for PCT/US2013/068506, dated Apr. 9, 2014.

International Search Report for PCT/US14/60122, dated Jan. 21, 2015.

International Preliminary Report on Patentability for PCT/US13/77234, dated Jun. 30, 2015.

International Search Report for PCT/US16/66671, dated Apr. 20, 2017.

International Search Report for PCT/US14/35051, dated Sep. 5, 2014.

(56) References Cited

OTHER PUBLICATIONS

International Search Report for PCT/US09/31228, dated Jun. 19, 2009.
International Search Report for PCT/US17/21456, dated Jun. 21, 2017.
International Search Report PCT/US08/85062, dated Mar. 20, 2009, XCorporeal, Inc.
International Search Report for PCT/US10/20698, Xcorporeal, Inc., dated Jun. 16, 2010.
International Search Report for PCT/US09/59906, Xcorporeal, Inc., dated May 8, 2012.
International Search Report for PCT/US09/62840, Xcorporeal, Inc. dated Feb. 10, 2012.
International Search Report for PCT/US11/53184, Xcorporeal, Inc., dated Mar. 2, 2012.
International Search Report for PCT/US09/59907, Xcorporeal, Inc., dated Apr. 13, 2010.
International Search Report for PCT/US10/29500, Xcorporeal, Inc., dated Jul. 2, 2010.
V. Gura et al. "Technical Breakthroughs in the Wearable Artificial Kidney (WAK)", Clinical Journal of the American Society of Nephrology, vol. 4, No. 9, Sep. 1, 2009 (Sep. 1, 2009), pp. 1441-1448, XP055548016, ISSN: 1555-9041, DOI: 10.2215/CJN.02790409.
Kyungsoo Lee et al. "Pulse Push/Pull Hemodialysis: In Vitro Study on New Dialysis Modality With Higher Convective Efficiency", Artificial Organs, vol. 32, No. 5, May 8, 2008 (May 8, 2008), pp. 406-411, XP055549097, US, ISSN: 0160-564X, DOI: 10.111/j.15251594.2008.00561.x.
L.A. Pedrini et al: "Transmembrane pressure modulation in high-volume mixed hemodiafiltration to optimize efficiency and minimize protein loss", Kidney International, vol. 69, No. 3, Jan. 6, 2006 (Jan. 6, 2006), pp. 573-579, XP055548020, London, GB, ISSN: 0085-2538, DOI: 10.1038/sj.ki.5000110.

* cited by examiner

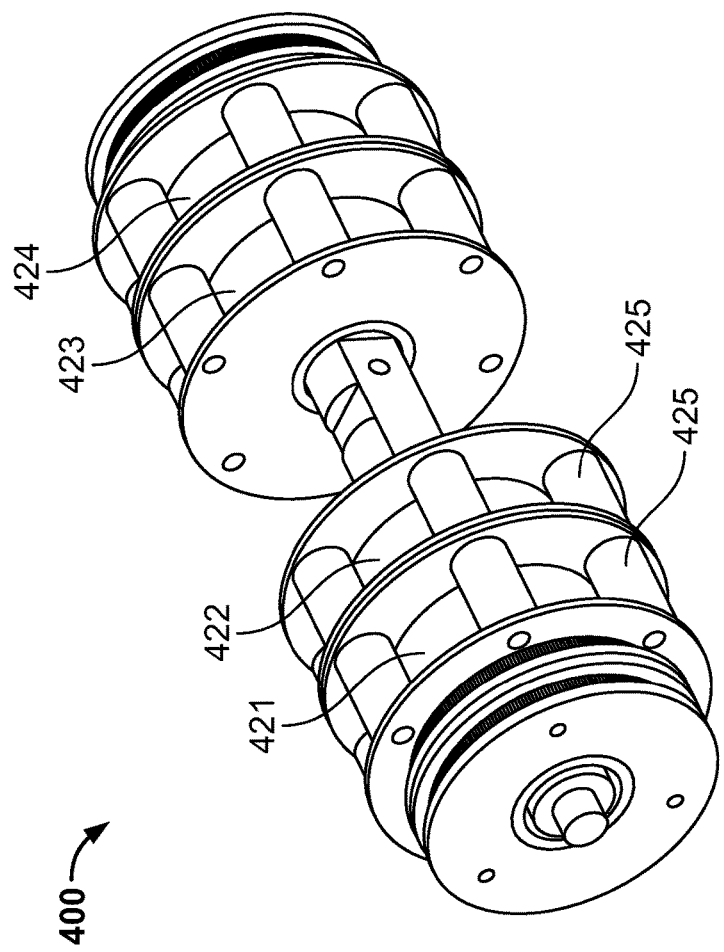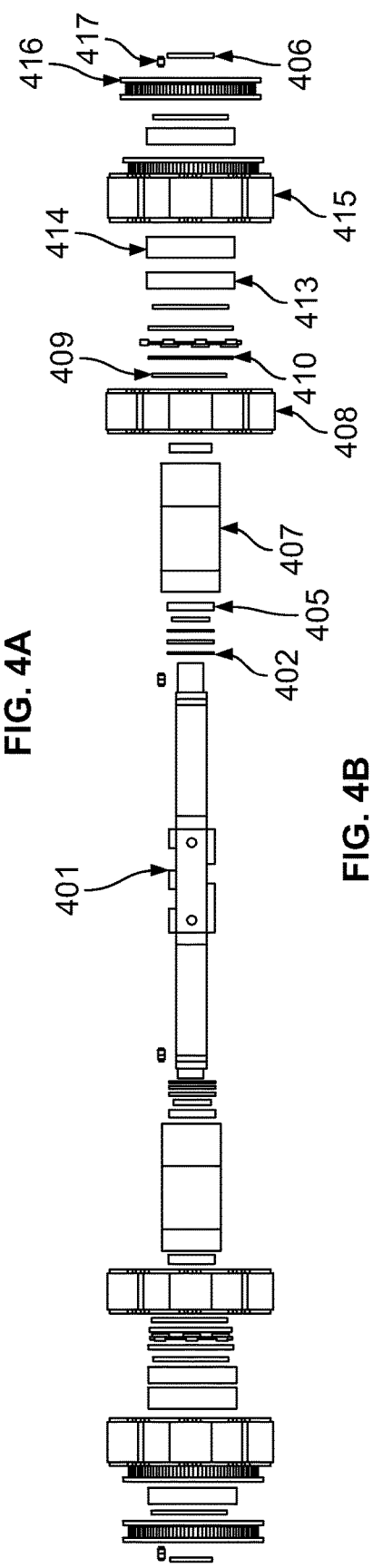
FIG. 4A
FIG. 4B

| Flow Rate (mL/min) | Post BP Min (mmHg) | Post BP Max (mmHg) | Min/Max Dur (ms) | Mean (mmHg) |
|---|---|---|---|---|
| 200 | -50 | 160 | 26 | 26 |
| 300 | -70 | 375 | 30 | 102 |
| 400 | -220 | 650 | 35 | 175 |
| 500 | -275 | 750 | 30 | 245 |

METHODS AND SYSTEMS OF GENERATING RAPIDLY VARYING PRESSURE AMPLITUDES IN FLUIDIC CIRCUITS IN A DIALYSIS TREATMENT SYSTEM

CROSS REFERENCE

The present specification relies on U.S. Patent Provisional Application No. 62/305,206, filed on Mar. 8, 2016, for priority, which is expressly incorporated herein by reference.

FIELD

The present specification relates generally to dialysis systems and more particularly, to hemofiltration systems with enhanced blood toxin clearance through varying pressure cycles generated within at least a blood circuit of the dialysis systems.

BACKGROUND

Blood purification systems, which are used for conducting hemodialysis, hemodiafiltration or hemofiltration, involve the extracorporeal circulation of blood through an exchanger having a semi-permeable membrane. Such systems further include a hydraulic system for circulating blood and a hydraulic system for circulating replacement fluid or dialysate including the certain blood electrolytes in concentrations close to those of the blood of a healthy subject.

Hemodialysis ("HD"), using a high flux membrane, removes toxins from the blood using transport mechanisms including diffusion and ultrafiltration (i.e., convective transport). Diffusion removes toxins using a concentration gradient across the semi-permeable membrane. For example, in a hemodialysis circuit, the dialysate solution flows on one side of the dialyzer membrane in one direction while simultaneously blood flows on the other side of the membrane. Ultrafiltration occurs when water (along with small solutes) is driven from the blood to dialysate in the dialyzer because of the hydrostatic pressure gradient between the blood and dialysate compartments (i.e., the transmembrane pressure ("TMP"). However, the small amount of waste removed by ultrafiltration during HD is not enough to provide convective clearance.

During hemofiltration ("HF"), a significant amount of ultrafiltration (more than is required to remove excessive fluid) is coupled with infusion of a replacement fluid to remove solutes. When compared to HD, HF achieves a higher removal of larger, poorly diffusible solutes, such as inulin (MW 5,200).

Hemodiafiltration ("HDF") is a treatment modality that combines convective and diffusive clearances. Like HD, HDF uses dialysate flowing through a dialyzer to provide a diffusive clearance. In addition, substitution solution is provided directly to the extracorporeal circuit, to provide convective clearance.

Most of the conventionally available blood purification systems are, however, quite bulky in size and difficult to operate. Further, the design of these systems makes them unwieldy and not conducive to the use and installation of disposable components. These conventional blood purification systems require a continuous supply of large amounts of fresh filtered water to create the dialysate fluid.

Another problem with existing dialysis machines is as these machines become smaller and a bit more portable, smaller hemofilters or dialyzer filters must be used that do not clog or clot too quickly so that extended or continuous dialysis can be performed. A common type of dialyzer includes several hundred or more cylindrical hollow fibers through which blood flow is provided. The hundreds of cylindrical hollow fibers are contained in a shell or container in which dialysate fluid is circulated around and past the exterior walls of the hollow fibers. The exterior walls of the hollow fibers or lumens are semi-porous so that impurities in the blood can be moved from the blood and into the dialysate. One problem that occurs in a dialyzer is the clogging or clotting of blood flow within individual hollow fibers. Such clogging of blood flow through the fibers decreases the effectiveness of the dialyzer's filtration and blood cleaning properties. Furthermore, it is understood that proteins and other compounds or substances in the blood may clog the pores of the semi-porous membrane overtime and decrease the effectiveness of the dialyzer filter.

Conventional systems and methods for improving the effectiveness of filtration of the dialyzer have been directed towards enabling a higher trans-membrane pressure ("TMP") gradient that is consistently positive, even at time scales less than 5 seconds, and does not cycle from negative to positive. For example, U.S. Patent Publication No. 20110139704 discloses a blood dialyzing apparatus that "includes a blood dialyzing filter for dialyzing blood by using a pressure difference between the blood and a dialysis solution, and a supplying means for supplying the blood and the dialysis solution to the blood dialyzing filter to alternately generate a state where a blood pressure is higher than a dialysis solution pressure and a state where the dialysis solution pressure is higher than the blood pressure. The blood dialyzing apparatus dialyzes a large volume of blood in a short period without increasing the size of the blood dialyzing filter and simply controls the volume of the dialyzed blood by adjusting the supply pressures of the blood and the dialysis solution."

U.S. Patent Publication No. 20110142700 discloses "a dual channel pulsatile pump for use with a completely wearable renal replacement device" such that "the pulsating flow of the exemplary dual channel pulsatile pump 1206 produces higher clearances than a continuous, steady, non-pulsating flow."

U.S. Patent Publication No. 20090120864 discloses a system that "uses two pulsatile pumps, a first pulsatile pump 301 for the blood circuit 310 and a second pulsatile pump 321 for the dialysate circuit 320. Prior art dialysis machines generate steady flow in both the blood circuit and the dialysate circuit. Some prior art dialysis machines use pulsatile flow in the blood circuit to more closely mimic the flow generated by a healthy heart but use steady flow in the dialysate circuit. In accordance with a novel feature, the dialysis system 300 of the present invention uses pulsatile flow in both circuits 310, 320 and runs the two pulsatile pumps 180 degrees out of phase so that the blood circuit pressure reaches a maximum when the dialysate circuit pressure reaches a minimum and vice versa. This pressure waveform periodically increases the trans-membrane pressure gradient in the dialyzer which adds convective mass transfer forces to drive fluid and waste exchange."

However, there is a need for a dialysis system that provides enhanced dialyzer clearance with reduced quantities of filtered water to create the dialysate. There is also a need for modulating pressure profiles within blood and/or dialysate circuits to generate desired pressure waveform characteristics for enhanced dialyzer clearance.

SUMMARY

The following embodiments and aspects thereof are described and illustrated in conjunction with systems, tools and methods, which are meant to be exemplary and illustrative, not limiting in scope. The present application discloses numerous embodiments.

Conventional hemofiltration ("HF") systems create a high convective force across the dialyzer using a large influx of water. This results in a transfer of larger sized molecules that are difficult or impossible to remove by diffusive transport alone. However, conventional HF systems pump significant amounts of filtered water (e.g., >15 L/treatment) into the blood circuit. This can be prohibitively expensive and raises safety concerns about the purity of the filtered fluid. The system of the present specification provides hemofiltration-like capabilities without requiring a large infusion of water, over and above the fluid required for dialysis itself, by generating and controlling a rapidly cycling pressure profile within the blood circuit. Specifically, the system of the present specification also generates and controls a varying pressure profile within the dialysate circuit to further enhance the dialyzer clearance.

In some embodiments, the present specification discloses a method for providing improved clearance levels of blood toxins in hemodialysis by generating a varying pressure profile in a fluid flow through a dialysis machine, said method including: providing a portable dialysis system including: a manifold, including a plurality of blood and dialysate circuits; at least one tube segment in fluid communication with at least one of said blood and dialysate circuits; and at least one pump for pumping a fluid through said at least one tube segment and at least one of said plurality of blood and dialysate circuits; and operating said at least one pump to apply a force to said at least one tube segment to generate fluid flow through said at least one tube segment, wherein said at least one pump is configured to generate said fluid flow with a pressure profile that varies between a positive pressure and a negative pressure within a predetermined period of time.

Optionally, said at least one pump includes a rotor pump having a plurality of rollers.

Optionally, said rotor pump has a diameter no greater than 4 inches.

Optionally, said rotor pump has a range of 4 to 6 rollers.

Optionally, each of said plurality of rollers includes a plurality of equidistantly spaced cylindrical pins.

Optionally, said plurality of equidistantly spaced cylindrical pins is in a range of 4 to 6.

Optionally, said fluid flow is any one of dialysate flow, blood flow, and infusate flow.

Optionally, a change in pressure amplitude experienced by said fluid flow is at least 100 mmHg and said predetermined period is less than 0.5 seconds.

Optionally, a change in pressure amplitude experienced by said fluid flow is at least 100 mmHg and said predetermined period is less than 0.05 seconds.

Optionally, a change in pressure amplitude experienced by said fluid flow is at least 200 mmHg and said predetermined period of time is less than 0.5 seconds.

Optionally, a change in pressure amplitude experienced by said fluid flow is at least 200 mmHg and said predetermined period of time is less than 0.05 seconds.

Optionally, an amplitude of said pressure profile varies from a positive 100 mmHg, or more, to a negative 25 mmHg, or less, over a period of time of less than 0.5 seconds.

Optionally, an amplitude of said pressure profile varies from a positive 100 mmHg, or more, to a negative 25 mmHg, or less, over a period of time of less than 0.05 seconds.

Optionally, an amplitude of said pressure profile varies from a positive 200 mmHg, or more, to a negative 50 mmHg, or less, over a period of time of less than 0.5 seconds.

Optionally, an amplitude of said pressure profile varies from a positive 300 mmHg, or more, to a negative 100 mmHg, or less, over a period of time of less than 0.5 seconds.

Optionally, a pressure amplitude of said fluid flow changes from positive pressure to negative pressure in less than 1 second and wherein a magnitude of the pressure amplitude change increases as the flow rate increases for the corresponding fluid flow.

Optionally, a pressure amplitude of said fluid flow changes from positive pressure to negative pressure in less than 1 second and a magnitude of the pressure amplitude change decreases as the flow rate decreases for the corresponding fluid flow.

Optionally, a pressure amplitude of said fluid flow cycles between a positive pressure and a negative pressure at least once in less than 0.5 seconds.

Optionally, a pressure amplitude of said fluid flow cycles between a positive pressure and a negative pressure at least twice in less than 0.5 seconds.

Optionally, a pressure amplitude of said fluid flow cycles between a positive pressure and a negative pressure at least three times in less than 0.5 seconds.

Optionally, the method further includes operating said at least one pump to fill said tube segment with said fluid at a first point in time such that said pressure profile reaches a maximum amplitude and operating said at least one pump to expel said fluid from said tube at a second point in time, occurring after said predetermined period of time, such that said pressure profile reaches a minimum amplitude.

The present specification also discloses a method for providing increasing clearance levels of blood toxins including providing a portable dialysis system comprising a manifold comprising a blood circuit, wherein said blood circuit has at least one tube segment; a rotor pump for pumping a blood through said at least one tube segment, wherein said rotor pump has a diameter no greater than 4 inches; and operating said at least one pump to apply a force to said at least one tube segment to generate blood flow through said at least one tube segment, wherein said at least one pump is configured to generate said blood flow with a pressure profile that varies between a positive pressure and a negative pressure within a predetermined period, wherein an amplitude of said pressure profile varies from a positive 100 mmHg, or more, to a negative 25 mmHg, or less, over a period less than 0.5 seconds and wherein an average pressure of said blood flow remains positive over a period of at least 5 seconds.

The present specification also discloses a dialysis system for providing increasing clearance levels of blood toxins including a manifold comprising a blood circuit, wherein said blood circuit has at least one tube segment; a rotor pump in physical communication with said at least one tube segment and configured to pump blood through said at least one tube segment, wherein said rotor pump has a diameter no greater than 4 inches; and a controller configured to operate said at least one pump to apply a force to said at least one tube segment to generate blood flow through said at least one tube segment, wherein said controller is adapted to control the at least one pump to generate said blood flow with a pressure profile that varies between a positive pressure and a negative pressure within a predetermined period.

Optionally, the dialysis system further includes a single fluid reservoir having a fluid capacity no greater than 10 liters. Optionally, the rotor pump has a range of 4 to 6 rollers. Optionally, the blood toxins include compositions having a molecular weight greater than 500 Daltons.

Optionally, the change in pressure amplitude experienced by the blood flow is at least 100 mmHg and said predetermined period is less than 0.5 seconds. The change in pressure amplitude experienced by the blood flow is at least 100 mmHg and said predetermined period is less than 0.05 seconds. The change in pressure amplitude experienced by the blood flow is at least 200 mmHg and said predetermined period is less than 0.5 seconds. The change in pressure amplitude experienced by the blood flow is at least 200 mmHg and said predetermined period is less than 0.05 seconds. The amplitude of the pressure profile varies from a positive 100 mmHg, or more, to a negative 25 mmHg, or less, over a period less than 0.5 seconds. The amplitude of the pressure profile varies from a positive 100 mmHg, or more, to a negative 25 mmHg, or less, over a period less than 0.05 seconds. The amplitude of the pressure profile varies from a positive 200 mmHg, or more, to a negative 50 mmHg, or less, over a period less than 0.5 seconds. The amplitude of the pressure profile varies from a positive 300 mmHg, or more, to a negative 100 mmHg, or less, over a period of less than 0.5 seconds. The pressure amplitude of the blood flow changes from positive pressure to negative pressure in less than 1 second and a magnitude of the pressure amplitude change increases as the blood flow rate increases for the corresponding blood flow. The pressure amplitude of the blood flow changes from positive pressure to negative pressure in less than 1 second and a magnitude of the pressure amplitude change decreases as the blood flow rate decreases for the corresponding blood flow. The pressure amplitude of the blood flow cycles between a positive pressure and a negative pressure at least once in less than 0.5 seconds. The pressure amplitude of the blood flow cycles between a positive pressure and a negative pressure at least twice in less than 0.5 seconds. The pressure amplitude of the blood flow cycles between a positive pressure and a negative pressure at least three times in less than 0.5 seconds. The amplitude of the pressure profile varies from a positive 100 mmHg, or more, to a negative 25 mmHg, or less, over a period less than 0.5 seconds and wherein an average pressure of said blood flow remains positive over a period of at least 5 seconds.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 4*a* is a schematic view of an exemplary rotor pump with four rotors, according to one embodiment;

FIG. 4*b* is an exploded view of the rotor pump of FIG. 4*a*;

DETAILED DESCRIPTION

Figure 1:
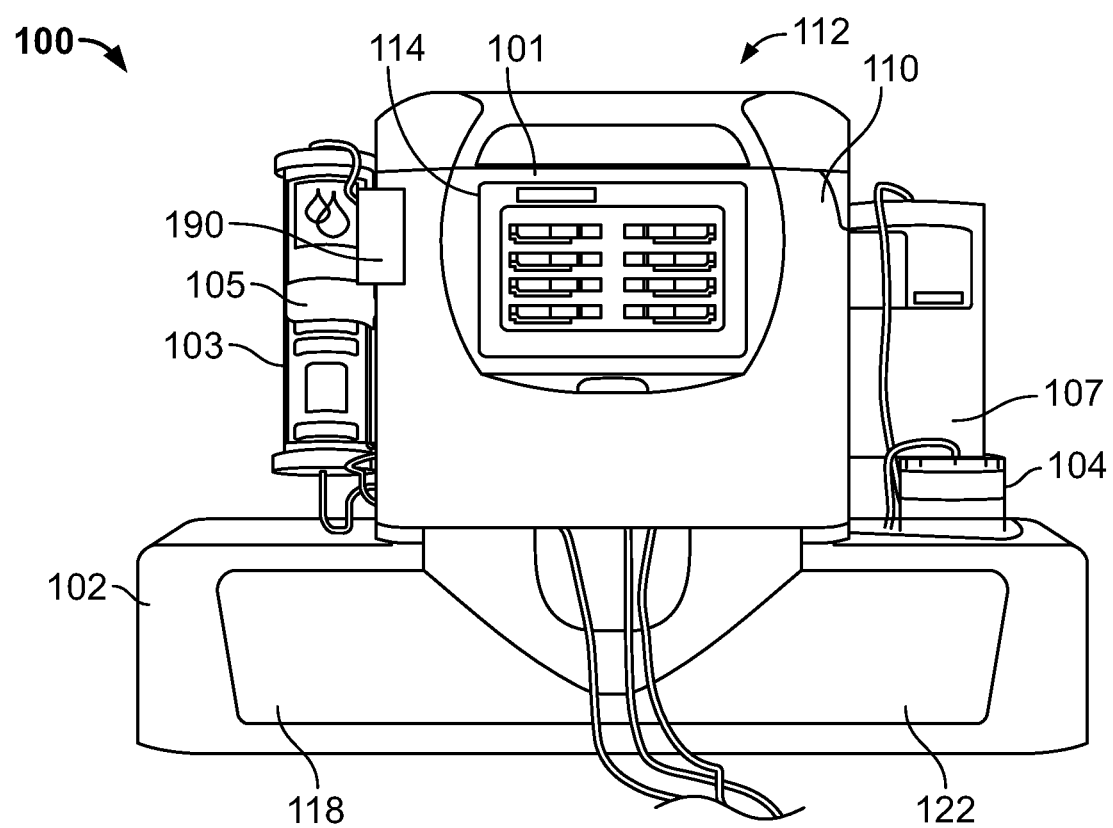
FIG. 1 is a front view of one embodiment of a dialysis system of the present specification.

The embodiments of the present specification are directed towards a dialysis system, and more specifically to a hemofiltration system, that is modular and portable, with improved clearance levels of blood toxins. In accordance with an aspect, embodiments of the present specification use at least one roller pump that is designed and operated to generate a varying pressure profile of fluid within at least a portion of the blood circuit of the dialysis system. The enhanced clearance of toxins from blood that occurs in embodiments of the present specification is achieved in part by application of a push/pull effect, particularly on mid-sized toxins or molecules, created by the varying pressure profile of blood (and optionally that of the dialysate) generated by the pumping action and the resulting transmembrane pressure ("TMP") across the semi-permeable membrane.

The systems and methods of the present specification are directed toward enhancing the clearance of toxins from the blood while providing certain advantages over current systems. Specifically, the dialyzer material used in systems of the present specification does not need to be modified (e.g. changing dialyzer permeability) to improve clearance capabilities. The systems of the present specification do not require redundant components (e.g. dialyzers in sequence) or extra components (e.g. substitution fluid sources or sub-station circuits) to enhance clearance. In addition, using a single dialyzer in the blood circuit provides HD and HF-like treatment without using a substitution fluid. By generating a negative-positive pressure cycle using existing blood and/or dialysate pumps, the systems and methods of the present specification achieve these advantages without requiring additional components in order to create a high pressure convective trans-membrane force.

In particular, the presently disclosed methods and systems generate a convective force within the blood and/or dialysate circuit, thereby resulting in an ability to remove middle to larger sized toxins, such as $\beta_2$ microglobulin and those compositions with a molecular weight of greater than 500 Daltons, including compositions with a molecular weight between 500 and 50,000 Daltons, from blood via a dialyzer. This is accomplished without requiring additional water, other than the 6-8 liters of water required for a conventional dialysis treatment, and specifically using less than the 15 liters, and preferably less than 10 liters, of water typically required by prior art systems. Accordingly, the presently disclosed embodiments can be practiced in dialysis systems having a single fluid reservoir with a fluid capacity of no greater than 10 liters (and preferably no greater than 8 or 9 liters), a single dialyzer, and no separate pump for a water ultrafiltrate supply conventionally required to generate the hydrostatic forces necessary for convection.

The present specification is directed towards multiple embodiments. The present disclosure is provided to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

It should be noted herein that any feature or component described in association with a specific embodiment may be used and implemented with any other embodiment unless clearly indicated otherwise As used herein, the terms "roller" and "rotor" are used interchangeably. Further, the terms "rotor pump" and "roller pump" are used interchangeably. Referring to FIG. 1, in one implementation, the dialysis system 100 includes a top unit 101 that is detachably affixed to a base 102. The base 102 includes a reservoir 122 for fluid storage, measurement, and monitoring. The top unit 101 also referred to as the main unit or controller unit, includes a graphical user interface 114, pumping unit, and a door 110 with a power lock and mechanical backup mechanism.

To a first side of the top unit 101 is a clasp 105 used to detachably affix a dialyzer 103. To a second, opposing side of the top unit 101 is a sorbent cartridge locking base 104 used to detachably affix a sorbent cartridge 107. It should be appreciated that the clasp 105, dialyzer 103, sorbent cartridge locking base 104 and sorbent cartridge 107 can also be positioned on the same side of the top unit 101. In either case, the bottom unit 102 has a sufficiently larger area relative to the top unit 101 such that shelves are formed on either side of the top unit 101 to hold the sorbent cartridge 107, to hold an infusate jar, to capture any spillage, and/or to channel any leaks into a leak detector.

Between the dialyzer 103 and door 110 are anti-coagulant pumps in the form of syringe pumps 190. Optionally, the top unit 101 can include a bottle holder that has a spiked base to receive a bottle, top-down, within the bottle holder housing. Infusion lines are connected to the inlet of the blood pump, outlet of the blood pump, or outlet of the dialyzer (blood side). The infusion lines could also 'thread' through air bubble detectors to sense if/when the anti-coagulant is emptied or blocked.

Figure 2:
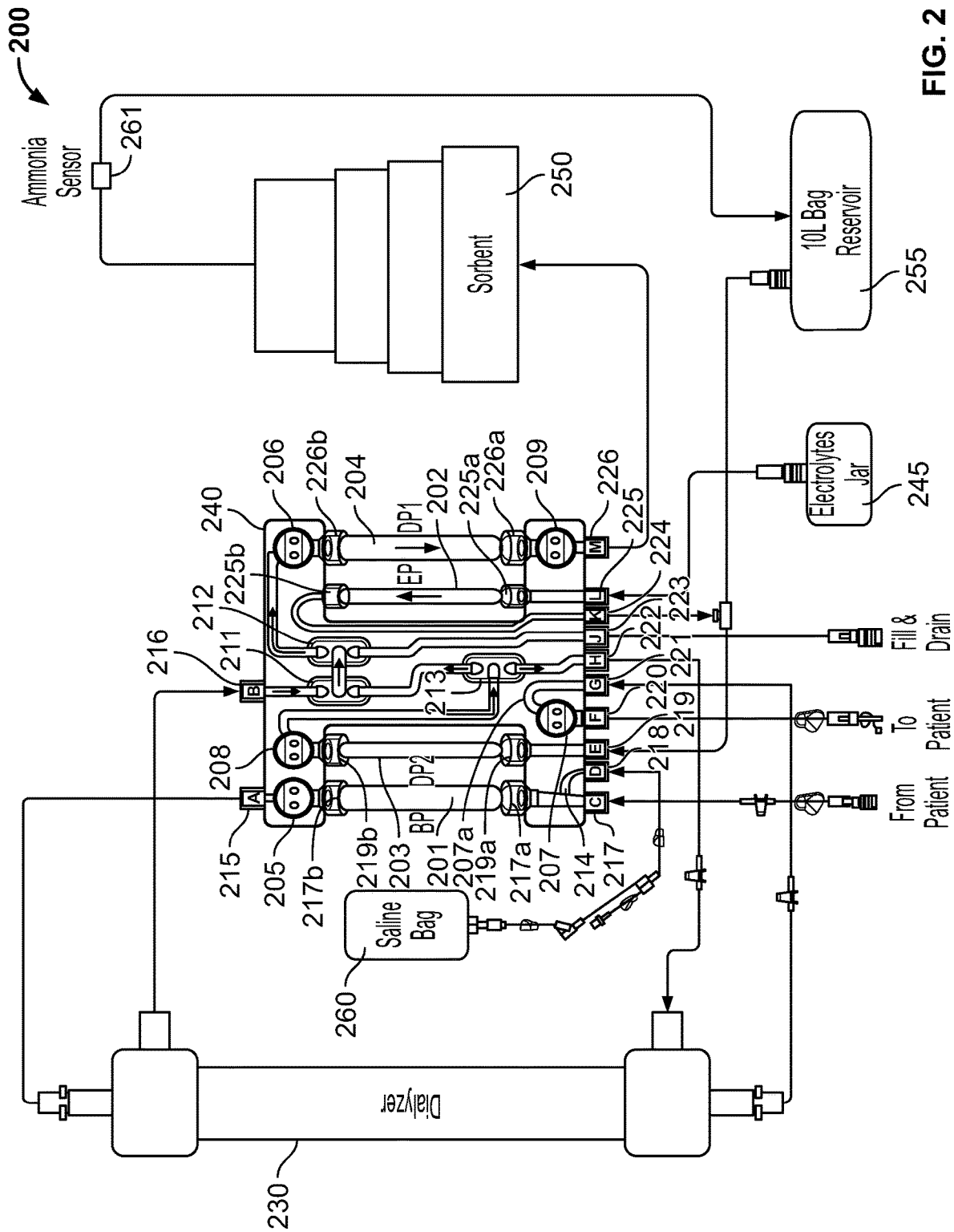
FIG. 2 is a functional block diagram of fluidic circuits of one embodiment of the dialysis system of FIG. 1 used for conducting hemodialysis and hemofiltration in accordance with an aspect of the present specification.

FIG. 2 is a functional block diagram of fluidic circuits of one implementation of a multiple-pass sorbent-based dialysis system 200 of the present specification used for conducting hemodialysis and hemofiltration. In accordance with an implementation, the system 200 is implemented within, and by, a plurality of blood and dialysate circuits molded into a manifold 240. The manifold 240 can be disposable. The fluidic circuit of the system 200 includes four pump tube segments 201, 202, 203 and 204 in pressure communication with pumps within a top unit (101 of FIG. 1) of the dialysis system. It further includes five pressure membranes in pressure communication with pressure sensors 205, 206, 207, 208 and 209. In the embodiment illustrated in FIG. 2, three two-way valves 211, 212 and 213 (each comprising a pair of membranes) are integrated into the manifold 240. The two-way valves 211, 212 and 213 function as valves when they are occluded by a pin, member or protrusion from the top unit (101 of FIG. 1).

Grouped in this manner, the pairs of membranes form three two-way valves 211, 212 and 213. The two-way valves provide greater flexibility in controlling the configuration of a circuit. When conventional two-way valves are used to occlude portions of a fluid pathway, they are typically configured to enable two different fluid pathways, one for a first valve state and one for the second valve state.

The pump tube segments 201, 202, 203, 204 are bonded into the compact manifold 240. A number of ports are provided in the manifold 240, which connect with tubes external to the manifold 240 to allow the flow of various fluids in and out of the manifold 240. These ports are connected to various tubes in the dialysis system 200 for carrying fluids as follows:

Port A 215—blood to the dialyzer 230,
Port B 216—dialyzer output (used dialysate);
Port C 217—blood from the patient;
Port D 218—saline (from saline/heparin source 260) for rinse back;
Port E 219—fresh dialysate reservoir 255 output (fresh dialysate);
Port F 220—patient return (clean blood);
Port G 221—dialyzer output (blood);
Port H 222—dialyzer input (fresh dialysate);
Port J 223—connects to prime and drain line;
Port K 224—infusate out/input to infusate reservoir 245;
Port L 225—infusate in from infusate reservoir 245;
Port M 226—dialysate flow into dialysate regeneration system 250.

In one implementation, a tube segment 214, formed as a pathway molded into the manifold 240, connects the fluid flow of saline, entering via Port D 218, to the flow entering via Port C 217. It should be appreciated that in alternate embodiments, the tube segment 214 connects a fluid flow of an anticoagulant, such as heparin, entering via Port D 218 to the fluid flow of blood entering via Port C 217. In such alternate embodiments, the bag 260 contains heparin instead of saline fluid. In some embodiments, the combined heparin and blood flow through port 217a, via pump tube segment 201, and into port 217b of the manifold 240. The pressure sensor or transducer 205 formed in the manifold 240, in turn, passes the blood and heparin fluid through Port A 215. Fluid flows out of the manifold 240 at Port A 215 passes through dialyzer 230, which is external to the manifold 240. The dialyzed blood passes back into the manifold 240 through Port G 221 and into a segment 207a, formed as a pathway molded into the manifold 240 that is in physical communication with the pressure sensor 207. Fluid then passes from the segment 207a through Port F 220 and into a patient return line.

Separately, dialysis fluid enters the manifold 240 from a dialysate reservoir 255 via Port E 219. The reservoir 245 has infusate in it, which first enters the manifold 240 via Port L 225, passes through a segment, formed as a pathway molded into the manifold 240, through another port 225a, through the pump tube segment 202 in communication with a pump, and back into the manifold 240 via port 225b. The infusate passes through another segment, formed as a pathway molded into the manifold 240, and out the manifold 240 at Port K 224. The fresh dialysate fluid which entered the manifold via Port E 219, passes through a segment formed as a pathway molded into the manifold 240, through another port 219a, through the pump tube segment 203 in communication with a pump, and back into the manifold 240 via port 219b.

The fresh dialysate fluid passes into a segment, formed as a pathway molded into the manifold 240, which is in physical communication with the pressure sensor 208 at one end and a pair of valves 213 at the other end. The fresh dialysate fluid passes out of the manifold 240 through Port H 222, and into a line that passes into the dialyzer 230.

A line out of the dialyzer 230 passes spent dialysate back into the manifold 240 through Port B 216 and into a segment, formed as a pathway molded into the manifold 240, that is in physical communication with a first pair of valves 211, a second pair of valves 212, and the pressure sensor 206. The used dialysate fluid passes out of the manifold 240 through port 226b, through the pump tube segment 204 in communication with a pump, and back into the manifold via port 226a. A segment in fluid communication with the port 226a is in physical communication with pressure transducer 209 and passes fluid through Port M 226 and to the dialysate regeneration system 250. In various embodiments, the ports are designed for circuit tubing in a range of 0.1" to 0.4"×0.05" to 0.3", more preferably 0.265"×0.180", or anticoagulant/saline and infusate tubing 0.05" to 0.3"×0.05" to 0.3", more preferably 0.165"×0.110".

The fresh or regenerated dialysate is output from the dialysate regeneration system 250 to the fresh dialysate reservoir 255 via an ammonia sensor 261. The dialysate regeneration system 250 includes a plurality of cartridges and/or filters containing sorbents for regenerating the spent dialysate. By regenerating the dialysate with sorbent cartridges, the dialysis system 200 uses a small fraction of the amount of dialysate of a conventional single-pass hemodialysis device.

In one implementation, each sorbent cartridge in the dialysate regeneration system 250 is a miniaturized cartridge containing a distinct sorbent. For example, the dialysate regeneration system 250 may employ five sorbent cartridges, wherein each cartridge separately contains activated charcoal, urease, zirconium phosphate, hydrous zirconium oxide and activated carbon. In another embodiment, each cartridge may include a plurality of layers of sorbents described above and there may be a plurality of such separate layered cartridges connected to each other in series or parallel in the dialysate regeneration system. Persons of ordinary skill in the art would appreciate that activated charcoal, urease, zirconium phosphate, hydrous zirconium oxide and activated carbon are not the only chemicals that could be used as sorbents in the present specification. In fact, any number of additional or alternative sorbents, including polymer-based sorbents, could be employed without departing from the scope of the present specification.

Figure 3:
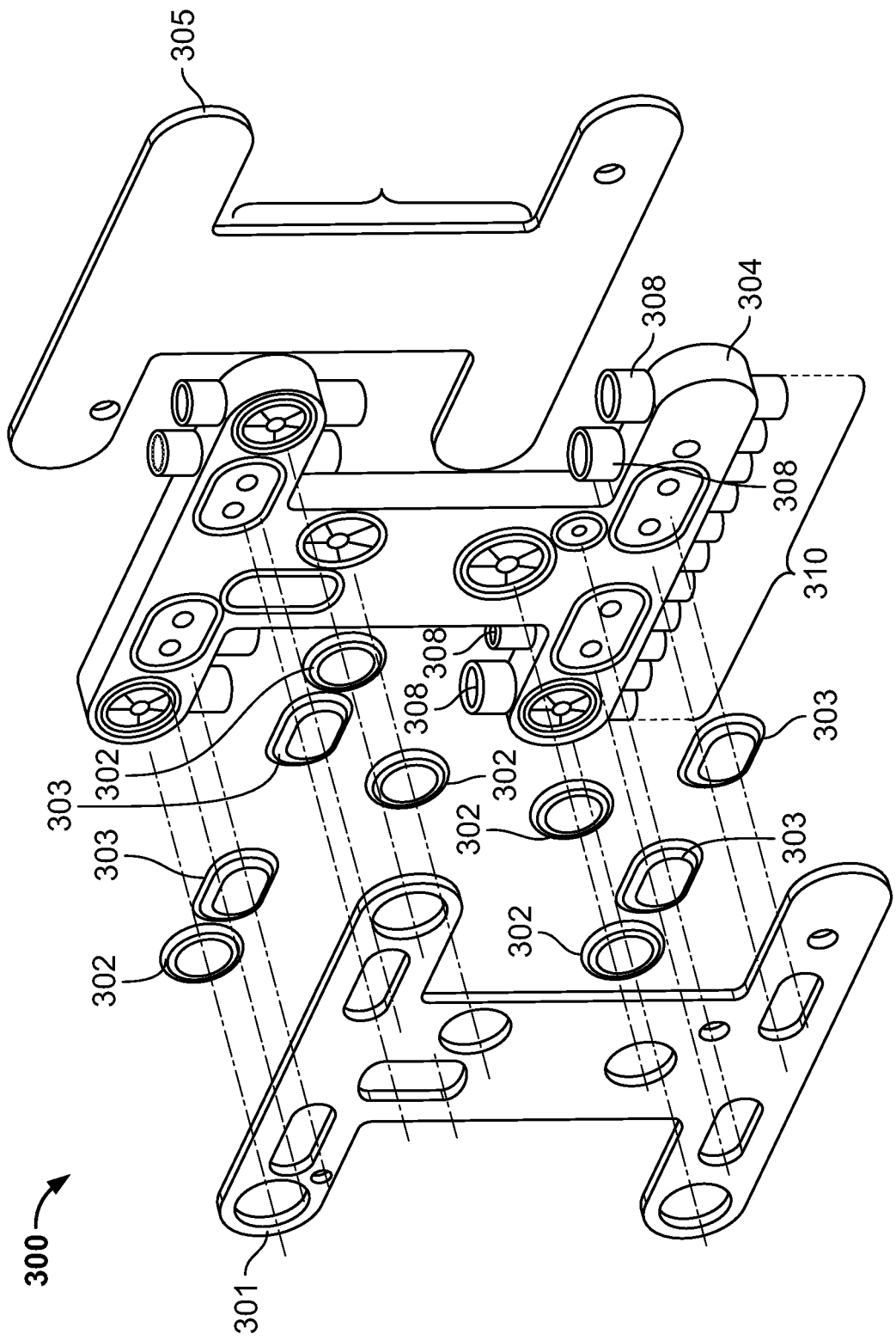
FIG. 3 is a schematic view of one embodiment of an exemplary manifold.

In one implementation, the manifold 240 includes a composite plastic manifold, into which the blood and dialysate flow paths are molded. Dialysis system 200 components, such as sensors and pumps, are placed into pressure, thermal, and/or optical communication with the fluid flow contained within the molded manifold 240. FIG. 3 illustrates structural elements of a compact manifold, according to one implementation. The disposable manifold pumps and directs fluid flow while measuring pressure in key areas. The key areas are indicative of pressure at critical points in the blood or dialysate circuits and equate to pressure sensors 205, 206, 207, 208, and 209 and, particularly to pressure at the dialyzer input (205). Those fluids include blood, dialysate, infusate and anticoagulant/saline. In addition, the manifold provides features for detecting blood leakage from the dialyzer, detecting an occlusion in the arterial line, and detecting air in the venous line.

Referring to FIG. 3, in one implementation, the compact manifold 300 includes a plurality of plastic layers with components fixedly attached therein. More specifically, the manifold 300 includes the following elements: back cover 301, pressure transducer membranes 302, valve membranes 303, mid-body 304, front cover 305, and pumping components 308.

The mid-body 304 contains molded in channels on one side. These channels are completed by the front cover layer which is fixedly attached to the mid-body by any number of methods, including ultrasonic welding. This combined front cover-mid-body structure forms the major part of the fluid pathways within the manifold. On the opposite side of the mid-body 304, there are features that form surfaces for valving and pressure sensing, which communicate to the fluid pathways on the front cover side of the manifold. The manifold includes elastomeric components for valving and pressure sensing. These elastomeric components are captured between the back cover layer and mid-body layer through the use of ultrasonic welding and complete the fluid pathways throughout the manifold.

In one implementation, the manifold 300 includes five pressure transducer membranes 302 and three to four membranes 303 for two-way valves. In one implementation, the two covers 301 and 305, and mid-body 304 of the manifold 300 are molded of a polycarbonate material or ABS (acrylonitrile butadiene styrene). The pressure transducer membranes 302 and valve membranes 303 are molded of a common material, such as Santoprene, or more preferably Sarlink, which is a medical grade elastomeric polymer. In one implementation front and back covers 305 and 301 may be molded of optically clear material, at least transparent to certain preselected wavelengths of light, to allow for spectroscopic analysis of the fluid(s) contained within.

Additionally, the manifold preferably includes four pumping components 308. These pumping components 308 are segments of extruded polyvinyl chloride (PVC") tubing formulated and dimensioned to have properties optimized for pump use, particularly roller pump use. This tubing is bonded to barbed fittings that are integrally molded to the manifold mid-body. One of the four pumping components is for drawing blood from the patient's artery and pumping it through a dialyzer and back to the patient's vein. Two pumping components are for dialysate flow and one is for infusate delivery to the dialysate fluid circuit. A separate syringe pump can be used for pumping anticoagulant/saline into the arterial blood pathway, pre-dialyzer.

In one implementation, the manifold further incorporates tubing ports 310, preferably in the range of 10-14 and more preferably 12 ports (corresponding to Ports A through M of FIG. 2), for connecting all the fluid pathways within the manifold to other components in the disposable set including dialyzer, sorbent cartridge, bag reservoir, infusate container, patient blood lines, anticoagulant/saline, sensors, priming line and drain.

Referring back to FIG. 2, the valve 213 is positioned substantially below and centered between the valves 211, 212. However, it should be appreciated that the 2-ways valves 211, 212, 213 can be positioned in different locations within the manifold 240 in alternate embodiments. In one implementation, the 2-way valves operate by having valve actuators, which are mounted on the instrument, compress an elastomeric diaphragm over a volcano seal to prevent dialysate flow through its respective pathway, as described in further detail below. The volcano seal opening is sized to match the channel geometry. In one implementation, the cross-sectional pathway through the interior of the valve is at least equivalent to 0.190" diameter when valves are open. When the valve is in the closed position, the valve actuator and elastomeric diaphragm consume most of the fluid path space around the volcano seal minimizing the potential for air entrapment. There are raised plastic features on the mid-body (304 of FIG. 3) that minimize dead space within the fluid path as well as help prevent the diaphragm from collapsing around the center fluid path under negative pressure conditions. The elastomeric diaphragm has an o-ring feature around its perimeter that fits into a groove on the mid-body (304 of FIG. 3). The o-ring is compressed between the mid-body and back cover (301 of FIG. 3) to form a fluid tight seal. The design provides for approximately 30% compression on the o-ring. The 2-way valves 211, 212, 213 control the direction of dialysate flow through the manifold 240.

The manifold 240 contains structures that allow for fluid pressure monitoring across diaphragms through the use of pressure sensors 205, 206, 207, 208 and 209. These pressure sensors may be transducers. Fluid is allowed to flow from channels on the front cover (305 of FIG. 3) side of the mid-body through the inlet and outlet holes underneath the diaphragm on the back cover (301 of FIG. 3) side. The cross-sectional pathway through the interior of the pressure sensing structure is at least equivalent to 0.190". The interior pathway is designed to minimize air entrapment while providing adequate fluid contact with the diaphragm.

The valves and diaphragms can be made from a variety of different materials and by different processes. In one implementation, the elastomeric components are made from silicone. In another embodiment, the elastomeric components are made from a variety of thermoplastic elastomers. Two shot molding may be used to attach the valves and diaphragms to the back cover (301 of FIG. 3). Two shot molding of valves and diaphragms would remove the need to individually assemble these parts into the manifold 240, therefore, reducing labor costs and improve the quality of the manifold assembly.

Pumping components in the manifold design have been defined as PVC header tubing. These headers combined with rotary peristaltic pumping system provide the flow of blood, dialysate, and infusate. The circuit tubing material for dialysate, infusate, and anticoagulant/saline is preferably kink resistant, such as the tubing referred to as Colorite, Unichem 8011-02®, a TEKNIPLEX® company. In various embodiments, the tubing dimensions for the dialysate lines are in a range of 0.1" to 0.4"×0.05" to 0.3," more preferably 0.265"±0.003" outer diameter ("OD")×0.180"±0.003" inner diameter ("ID"), or anticoagulant/saline and infusate tubing 0.1" to 0.4"×0.05" to 0.3", more preferably 0.268" OD×0.175" ID.

Referring again to FIG. 2, in accordance with an implementation, at least four pulsatile roller pumps are employed. One of the at least four roller pumps is a blood pump which is in pressure communication with the pump tube segment 201 for enabling requisite blood flow through the blood circuit—that is, for drawing blood from the patient's artery and pumping it through the dialyzer 230 and back to the patient's vein. A second and a third of the at least four roller pumps is a fresh dialysate pump and a spent dialysate pump, which are in pressure communication with pump tube segments 203, 204 respectively, for effecting requisite dialysate flow through the dialysate circuit. A fourth of the at least four roller pumps is an infusate pump, which is in pressure communication with the pump tube segment 202 for enabling infusate delivery to the dialysate fluid circuit. As mentioned earlier, a separate syringe pump can be used for pumping anticoagulant/saline into the arterial blood pathway, pre-dialyzer.

In accordance with an aspect of the present specification, at least one of the four pulsatile roller pumps, such as the blood pump, is configured, designed and/or operated to generate a desired varying pressure profile of flow within the blood circuit of the dialysis system 200. The desired varying pressure profile is characterized by instantaneous pressure that goes through repeated, rapid cycles of positive and negative pressure at a given rate of flow. While the instantaneous pressure swings from high or positive and low or negative pressure, as further described below, the average or mean pressure remains positive and substantially constant over at least a 5 second period. It is preferred that the average pressure remains positive in order to make sure the flow is both in the appropriate direction, e.g. toward the dialyzer and not back flowing into the manifold, and not excessively turbulent, which may occur if the average pressure over 5 seconds or more is not substantially constant.

Thus, in various embodiments, to generate the desired varying pressure profile the blood pump of the present specification has a combination of following operational and design parameters: a flow rate greater than 200 mL/min, more specifically ranging from 200 mL/min to 500 mL/min; a pump speed ranging from 40 to 200 rotations-per-minute ("RPM"); a pump rotor size of no greater than 4.0 inches diameter; and number of rotors in the rotor pump ranging from 4 to 6.

FIG. 4a is a diagram illustrating an exemplary rotor pump 400 with four rotors 421, 422, 423 and 424. In an implementation, the rotors are disc shaped and rotate vertically. More specifically, the rotors are oriented within the dialysis machine such that the planar surface of the disc, or central area defined by the radius of the disc, is oriented vertically and perpendicular to the door of the dialysis machine. The edges of the rotors are therefore also oriented vertically and perpendicular to the door of the dialysis machine. Accordingly, when the rotors turn, they exert a force that presses against the manifold tubing, positioned parallel to the dialysis machine door and front panel and normal to the edges of the spinning rotors.

In an implementation, each of the four rotors includes a set of equidistantly spaced rollers 425, placed horizontally with respect to the rotors, in a range of four to six. The rollers exert pressure on the pump tube segments to help generate the desired varying pressure profile. The positive swing in the varying pressure profile is achieved as the rollers 425 come into contact with the manifold tubing, compressing the tubing and expelling fluid from the tubing. The negative swing in the varying pressure profile is caused as the rollers 425 move away from the tubing, allowing the tubing to expand and refill with fluid. In various embodiments, the frequency and degree of variation in the pressure profile is determined by the size of the rollers, number of rollers, and space between each roller. The diameter of the rollers influences the push/pull effect created by the pressure peaks of the varying pressure profile. For example, a roller having too large of a diameter will not produce the desired pressure peaks. In one implementation, the number of rollers in each rotor ranges from four to six. FIG. 4b provides a detailed illustration of the rotor pump of FIG. 4a. Referring to FIGS. 4a and 4b, at the center of the rotor pump is an axle shaft and pump drive mechanism 401. The pump drive is connected to a set of two peristaltic rotors 408. In one implementation each identical rotor in the set has a diameter in a range of 1 to 6 inches, preferably about 2.74 inches, and a width in a range of 0.2 to 2 inches, preferably about 0.825 inches. The pump drive is further connected to another set of two peristaltic rotors 415, each identical rotor in the set having a diameter in a range of 1 to 6 inches, preferably about 2.69 inches, and a width in a range of 0.2 to 3 inches, preferably about 0.925 inches, according to one implementation. The rotors 408, 415 are connected to the pump drive 401 by a coupling mechanism including a series of coupling elements including washers 402, 410, bearings 405, 413, hollow axles 407, retainers 406, 409, spacers 414, timing pulleys 416 and screws 417.

Figure 4C:
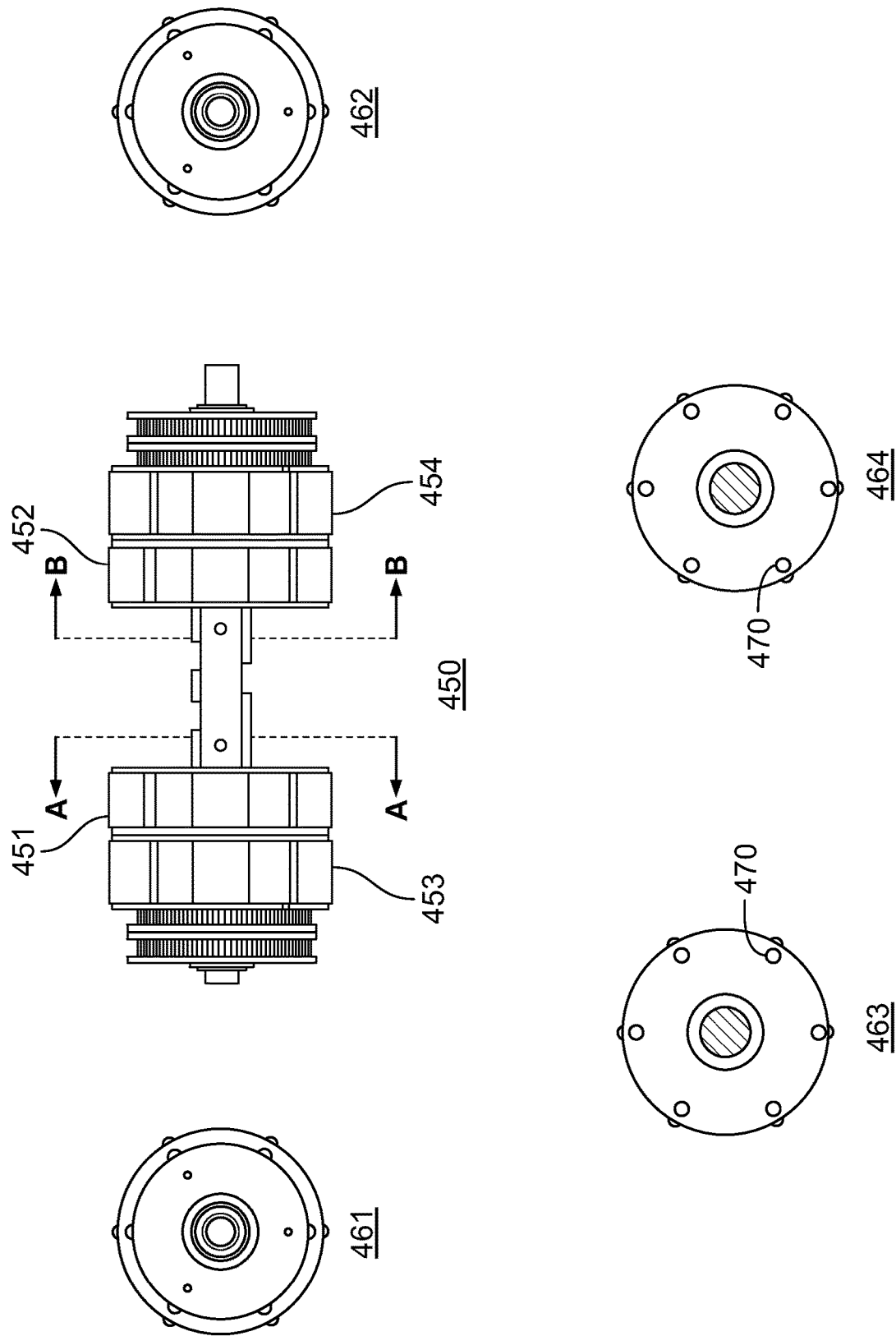
FIG. 4*c* is a cross-sectional diagram of the rotor pump, according to one embodiment.

FIG. 4c illustrates a cross-sectional diagram of the rotor pump 450. It may be noted that in one implementation, two of the peristaltic rotors 451, 452 are slightly larger in diameter than the other two rotors 453, 454, as also described above in their dimensions with respect to FIG. 4b. However, the inner radius of all the four rotors is the same and in the range of 0.1 to 1 inches, preferably 0.49 inches, as shown by 461, 462, 463 and 464, corresponding to the diameter of the axle and pump drive shaft that they are coupled to. It can further be seen in 461, 462, 463 and 464 that each rotor has holes 470 for fitting in a fixed number of rollers (not shown), which in this case is six.

Figure 10A:
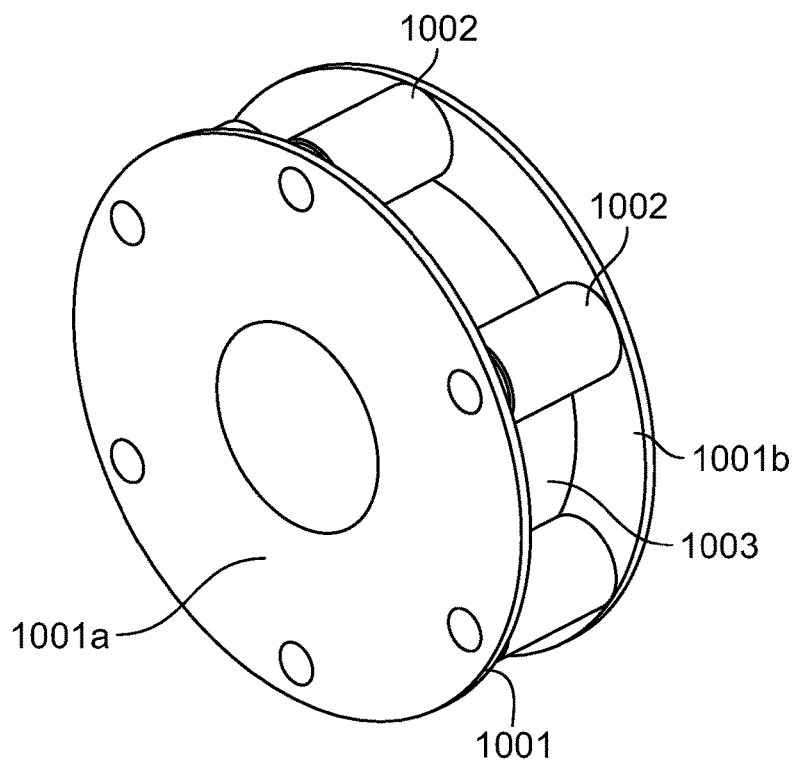
FIG. 10*a* illustrates a magnified view of a rotor of the rotor pump, according to one embodiment of the specification.
Figure 10B:
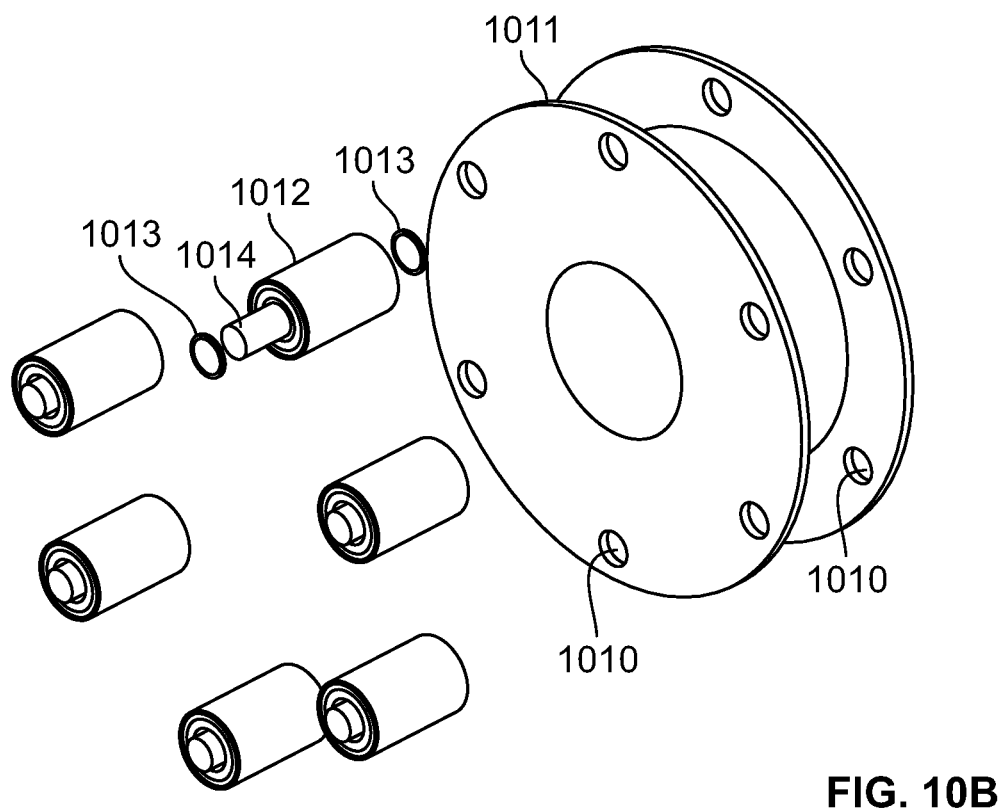
FIG. 10*b* illustrates a detailed view of the peristaltic rotor and the rollers, in accordance with one embodiment.

FIG. 10a illustrates a magnified view of a rotor of the rotor pump shown in FIG. 4a. Referring to FIG. 10a, a peristaltic rotor 1001 is disc shaped and includes six rollers 1002, equidistantly placed around the circumference of the rotor. Specifically, the peristaltic rotor 1001 includes two discs 1001a and 1001b, and a cylindrical segment 1003 connecting the two discs. The cylindrical segment 1003 allows the pump shaft to pass through the rotor. FIG. 10b illustrates a detailed view of the peristaltic rotor and the rollers. Referring to FIG. 10b, each disc in the rotor 1011 includes holes or slots 1010, for the placement of cylindrical rollers 1012. In this example, each rotor disc includes six holes around its edges for the placement of a corresponding number of rollers. In embodiments, each rotor of the pump may include holes for four to six rollers. In one implementation, each cylindrical roller 1012 includes a cylindrical pin 1014 placed inside. Cylindrical pins 1014 are sized according to dimensions of the holes 1010 in the rotor disc and are used to fit in the rollers into appropriate slots. In one implementation, the diameter of each cylindrical pin 1014 is around 5 mm. It may be noted that the rollers may be placed into their respective slots by screwing, threading, slip fitting or press fitting the cylindrical pins into the provided slots. In one implementation, a threadlocker (not shown) is applied to the ends of each cylindrical pin 1014, before press fitting into the holes of the rotor 1011. Bearing spacers 1013 are used to retain a proper fit of the cylindrical pins 1014, and of corresponding cylindrical roller 1012.

Figure 10C:
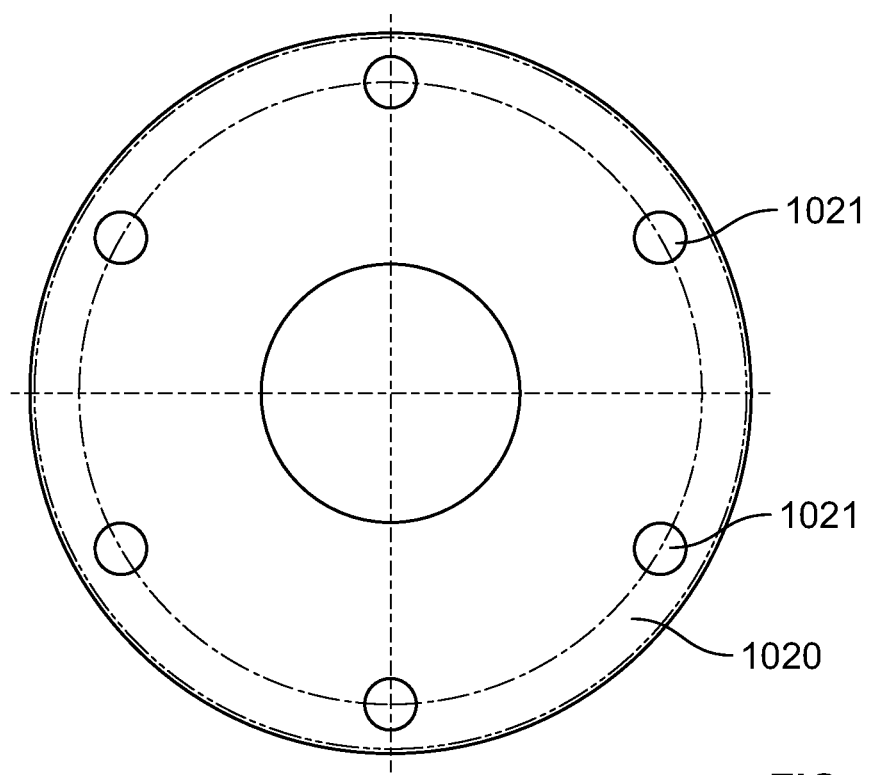
FIG. 10*c* illustrates a cross sectional diagram of the disc of a peristaltic rotor, in accordance with one embodiment of the present specification.

FIG. 10c illustrates a cross-sectional diagram of the disc of a peristaltic rotor 1020. In one implementation the diameter of the peristaltic rotor disc 1020 is about 2.740 inches. The peristaltic rotor disc 1020 includes six holes or slots 1021 around its edges. In one implementation, the six holes or slots 1021 are placed in a circle with a diameter of around 2.368 inches. In one implementation, the diameter of each hole is about 0.1969 inches for slip fitting a 5 mm cylindrical pin. In another embodiment, the diameter of each hole is about 0.1960 inches for press fitting a 5 mm cylindrical pin.

While in some embodiments, the desired varying pressure profile is generated only within the blood circuit by the blood pump, it should be appreciated that in various alternate embodiments similar pressure profiles may also be simultaneously generated within the dialysate circuit. In such embodiments, either one or both of the fresh and spent dialysate pumps may also have operational and design parameters similar to those of the blood pump of the present specification. In still further embodiments, along with the blood pump, additionally any one, two or all three of the fresh, spent and infusate pumps are designed and operated to generate the desired varying pressure profile within their corresponding fluid circuits.

Figure 5A:
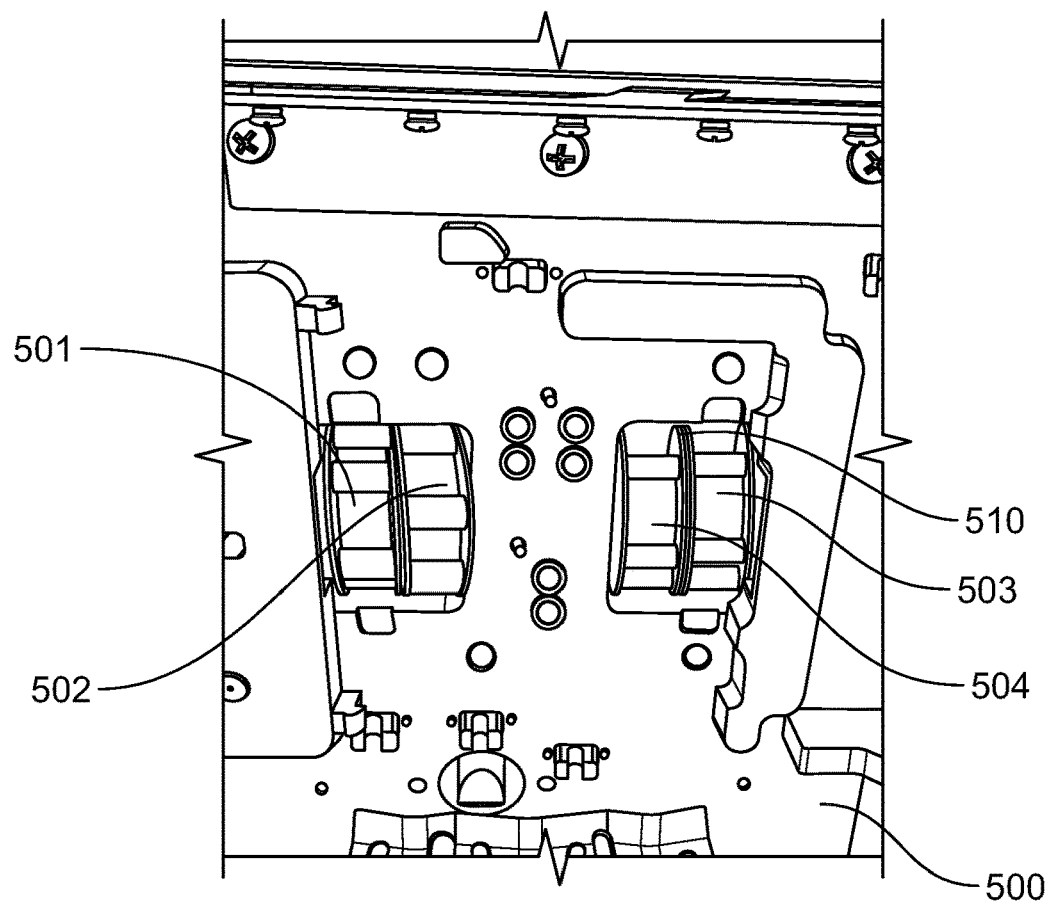
FIG. 5*a* is a view of the portable dialysis system of the present specification with a rotor pump installed.

FIG. 5a is a view of the portable dialysis system 500 of the present specification with a rotor pump 510 installed. It may be noted that FIG. 5a provides a view of the portable dialysis system without the tubing. Referring to FIG. 5a, rotor 501 of rotor pump is configured to apply force to a manifold pump segment to cause a fluidic motion of blood, while rotor 502 of the pump is configured to apply force to a manifold pump segment to cause a fluidic motion of fresh dialysate. Rotor 503 of the pump is configured to apply force to a manifold pump segment to cause a fluidic motion of spent dialysate and rotor 504 of the rotor pump 510 is configured to apply force to a manifold pump segment to cause a fluidic motion of infusate.

Figure 5B:
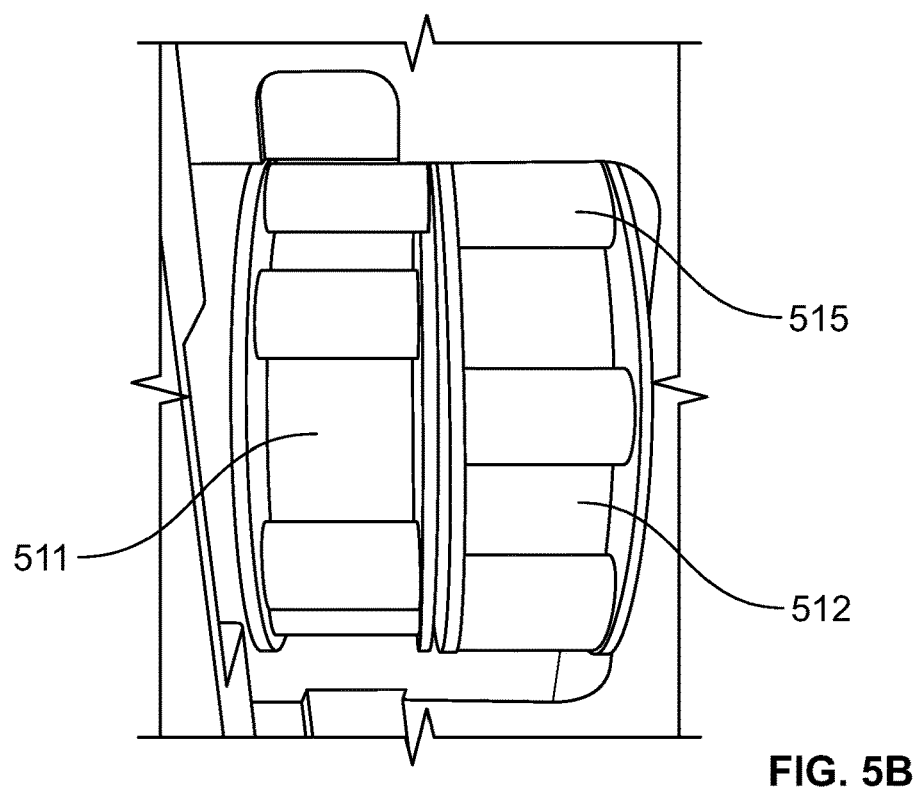
FIG. 5*b* is a close-up view of the portable dialysis system of the present specification showing rollers in an installed rotor pump, in accordance with one embodiment.

FIG. 5b provides a close view of two rotors 511 and 512 of a rotor pump, used for pumping blood and fresh dialysate, respectively. In an implementation, each of the two rotors includes six rollers 515.

Figure 6A:
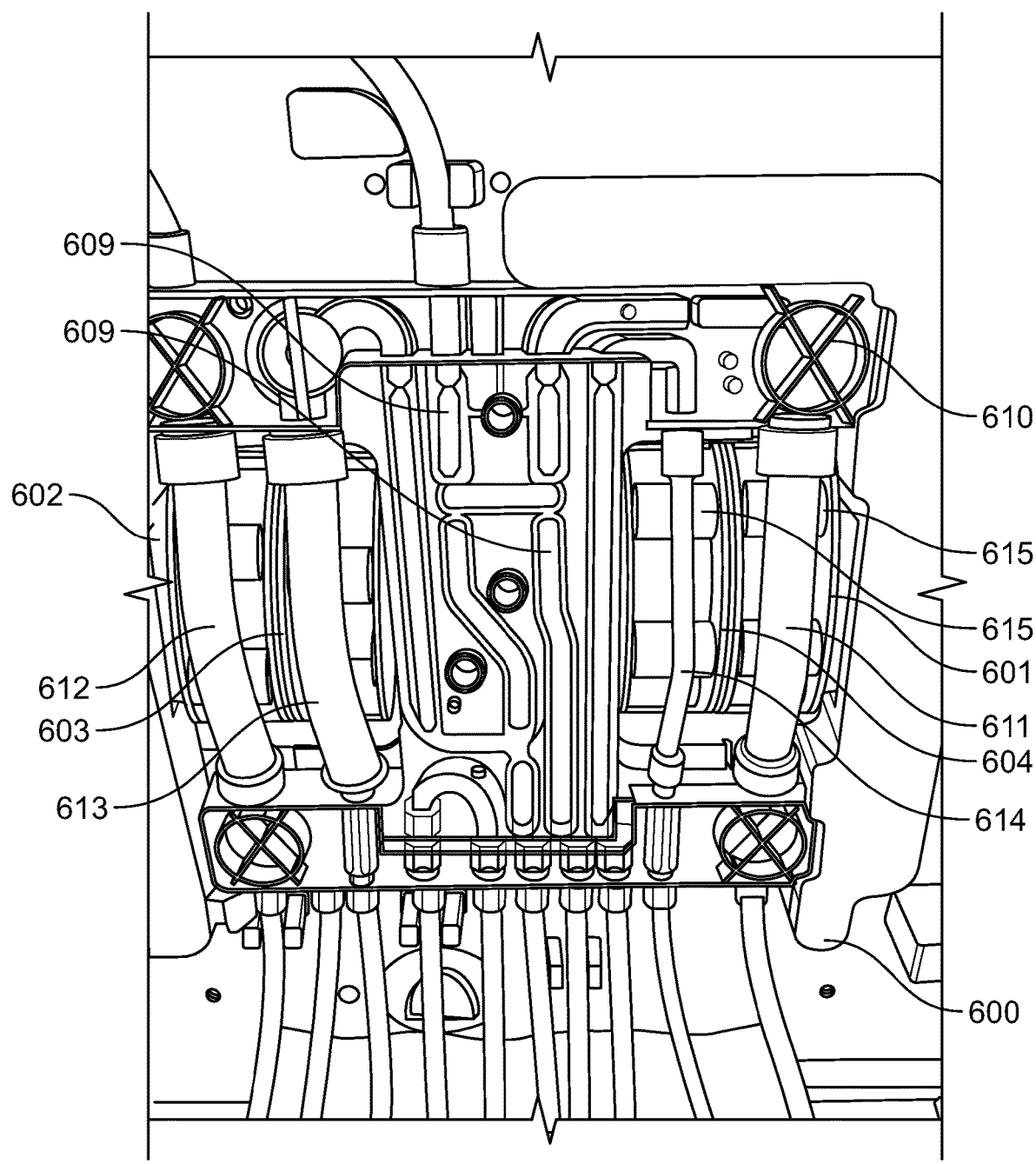
FIG. 6*a* is a view of a rotor pump installed in the portable dialysis system of present specification, along with the tubing and manifold.

FIG. 6a is a view of a rotor pump installed in the portable dialysis system of the present specification, along with the tubing and manifold, according to one implementation. Referring to FIG. 6a, the manifold 610 of the portable dialysis system 600 is compact and can be formed from a plastic material. As described earlier with reference to FIG. 3, the manifold 610 includes a plurality of plastic layers with components fixedly attached therein, including pump tube segments. Fluid pathways are molded in the form of channels 609 in the body of the manifold. A rotor pump with four rotors 601, 602, 603 and 604 is installed into the system. As can be seen from the figure, the rollers 615 in each of the roller pumps are placed such that they exert pressure on the tube segments 611, 612, 613 and 614, respectively.

Figure 6B:
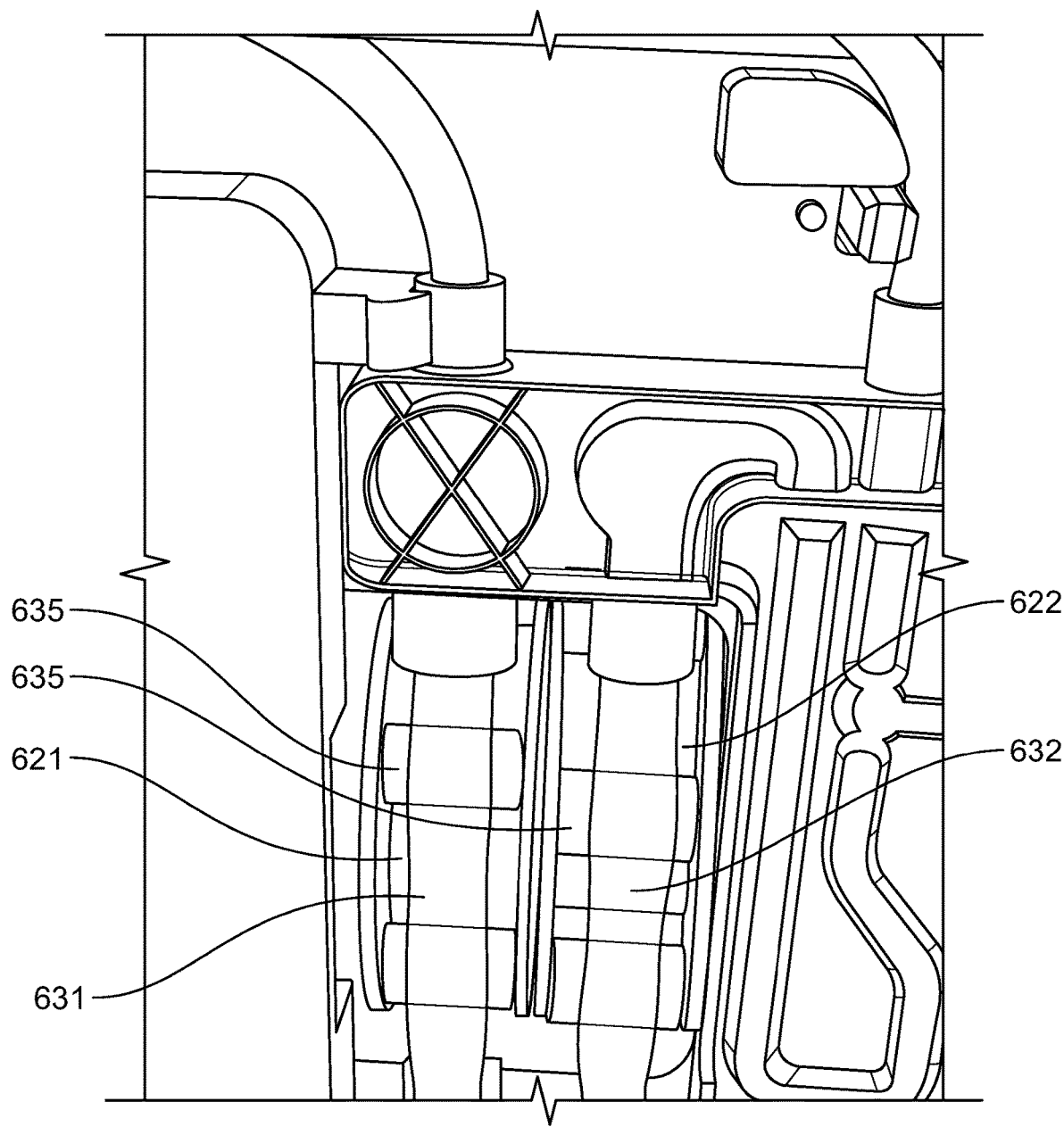
FIG. 6*b* provides a close-up view of the rollers in the installed rotor pump in the portable dialysis system of present specification, according to one embodiment.

FIG. 6b provides a close view of an installed rotor pump in the portable dialysis system of the present specification. Referring to FIG. 6b, the rollers 635 in the roller pumps 621 and 622 exert pressure on the manifold tubing, such that tube segments 631 and 632 are deformed due to the pressure.

Figure 7:
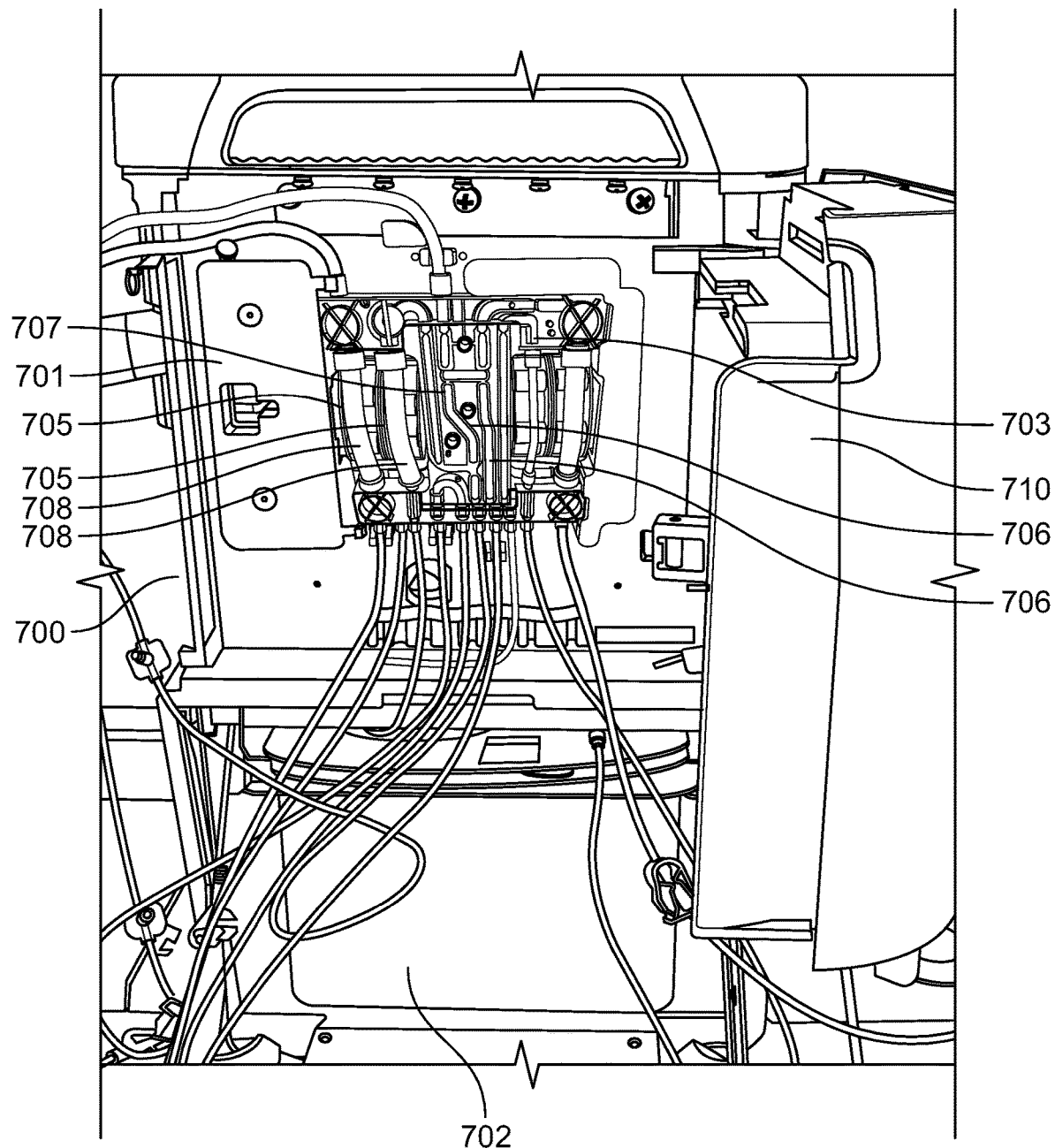
FIG. 7 illustrates one embodiment of the portable dialysis system with the rotor pump and tubing set.

FIG. 7 is a picture of the entire system with the rotor pump and tubing set, according to an implementation. Referring to FIG. 7, in one implementation, the dialysis system 700 includes a top unit 701 that is detachably affixed to a base 702. The top unit 701 also referred to as the main unit or controller unit, includes a graphical user interface (not shown), pumping unit 703, and a door 710 with a power lock and mechanical backup mechanism. The pumping unit further includes a rotor pump with a plurality of rotors 705—in this example four, which pump blood, fresh and spent dialysate and infusate through the requisite channels 706 of the manifold 707 and the corresponding tube segments 708.

Accordingly, in one implementation, a dialysis machine has between 2 and 6 rotors, each positioned such that the rollers which include the edges of each rotor are positioned against a tube segment of a manifold, and is operated to achieve a varying pressure profile for the flow of liquids through the manifold, dialyzer, sorbent cartridge and/or other components of the dialysis system, said liquids including dialysate, blood, and infusate. The varying pressure profile is preferably achieved by operating the pumps to achieve a flow rate greater than 200 mL/min, more specifically ranging from 200 mL/min to 500 mL/min with a pump rotor size of no greater than 4.0 inches diameter and a number of rollers ranging from 4 to 6. The varying pressure profile shall be defined in at least one of the following ways:

1. The change in pressure amplitude experienced by at least one of the dialysate flow, blood flow, and infusate flow is at least 100 mmHg over a period of time of less than 0.5 seconds anywhere along the fluidic circuit of the dialysate, blood, or infusate flow and particularly within the manifold.
2. The change in pressure amplitude experienced by at least one of the dialysate flow, blood flow, and infusate flow is at least 100 mmHg over a period of time of less than 0.25 seconds anywhere along the fluidic circuit of the dialysate, blood, or infusate flow and particularly within the manifold.
3. The change in pressure amplitude experienced by at least one of the dialysate flow, blood flow, and infusate flow is at least 100 mmHg over a period of time of less than 0.15 seconds anywhere along the fluidic circuit of the dialysate, blood, or infusate flow and particularly within the manifold.
4. The change in pressure amplitude experienced by at least one of the dialysate flow, blood flow, and infusate flow is at least 100 mmHg over a period of time of less than 0.1 seconds anywhere along the fluidic circuit of the dialysate, blood, or infusate flow and particularly within the manifold.
5. The change in pressure amplitude experienced by at least one of the dialysate flow, blood flow, and infusate flow is at least 100 mmHg over a period of time of less than 0.05 seconds anywhere along the fluidic circuit of the dialysate, blood, or infusate flow and particularly within the manifold.
6. The change in pressure amplitude experienced by at least one of the dialysate flow, blood flow, and infusate flow is at least 200 mmHg over a period of time of less than 0.5 seconds anywhere along the fluidic circuit of the dialysate, blood, or infusate flow and particularly within the manifold.
7. The change in pressure amplitude experienced by at least one of the dialysate flow, blood flow, and infusate flow is at least 200 mmHg over a period of time of less than 0.25 seconds anywhere along the fluidic circuit of the dialysate, blood, or infusate flow and particularly within the manifold.
8. The change in pressure amplitude experienced by at least one of the dialysate flow, blood flow, and infusate flow is at least 200 mmHg over a period of time of less than 0.15 seconds anywhere along the fluidic circuit of the dialysate, blood, or infusate flow and particularly within the manifold.
9. The change in pressure amplitude experienced by at least one of the dialysate flow, blood flow, and infusate flow is at least 200 mmHg over a period of time of less than 0.1 seconds anywhere along the fluidic circuit of the dialysate, blood, or infusate flow and particularly within the manifold.
10. The change in pressure amplitude experienced by at least one of the dialysate flow, blood flow, and infusate flow is at least 200 mmHg over a period of time of less than 0.05 seconds anywhere along the fluidic circuit of the dialysate, blood, or infusate flow and particularly within the manifold.
11. The pressure amplitude (experienced by at least one of the dialysate flow, blood flow, and infusate flow) varies from a positive 100 mmHg, or more, to a negative 25 mmHg, or less, over a period of time of less than 0.5 seconds anywhere along the fluidic circuit of the dialysate, blood, or infusate flow and particularly within the manifold.
12. The pressure amplitude (experienced by at least one of the dialysate flow, blood flow, and infusate flow) varies from a positive 100 mmHg, or more, to a negative 25 mmHg, or less, over a period of time of less than 0.25 seconds anywhere along the fluidic circuit of the dialysate, blood, or infusate flow and particularly within the manifold.
13. The pressure amplitude (experienced by at least one of the dialysate flow, blood flow, and infusate flow) varies from a positive 100 mmHg, or more, to a negative 25 mmHg, or less, over a period of time of less than 0.15 seconds anywhere along the fluidic circuit of the dialysate, blood, or infusate flow and particularly within the manifold.
14. The pressure amplitude (experienced by at least one of the dialysate flow, blood flow, and infusate flow) varies from a positive 100 mmHg, or more, to a negative 25 mmHg, or less, over a period of time of less than 0.1 seconds anywhere along the fluidic circuit of the dialysate, blood, or infusate flow and particularly within the manifold.
15. The pressure amplitude (experienced by at least one of the dialysate flow, blood flow, and infusate flow) varies from a positive 100 mmHg, or more, to a negative 25 mmHg, or less, over a period of time of less than 0.05 seconds anywhere along the fluidic circuit of the dialysate, blood, or infusate flow and particularly within the manifold.
16. The pressure amplitude (experienced by at least one of the dialysate flow, blood flow, and infusate flow) varies from a positive 200 mmHg, or more, to a negative 50 mmHg, or less, over a period of time of less than 0.5 seconds anywhere along the fluidic circuit of the dialysate, blood, or infusate flow and particularly within the manifold.

17. The pressure amplitude (experienced by at least one of the dialysate flow, blood flow, and infusate flow) varies from a positive 200 mmHg, or more, to a negative 50 mmHg, or less, over a period of time of less than 0.25 seconds anywhere along the fluidic circuit of the dialysate, blood, or infusate flow and particularly within the manifold.

18. The pressure amplitude (experienced by at least one of the dialysate flow, blood flow, and infusate flow) varies from a positive 200 mmHg, or more, to a negative 50 mmHg, or less, over a period of time of less than 0.15 seconds anywhere along the fluidic circuit of the dialysate, blood, or infusate flow and particularly within the manifold.

19. The pressure amplitude (experienced by at least one of the dialysate flow, blood flow, and infusate flow) varies from a positive 200 mmHg, or more, to a negative 50 mmHg, or less, over a period of time of less than 0.1 seconds anywhere along the fluidic circuit of the dialysate, blood, or infusate flow and particularly within the manifold.

20. The pressure amplitude (experienced by at least one of the dialysate flow, blood flow, and infusate flow) varies from a positive 200 mmHg, or more, to a negative 50 mmHg, or less, over a period of time of less than 0.05 seconds anywhere along the fluidic circuit of the dialysate, blood, or infusate flow and particularly within the manifold.

21. The pressure amplitude (experienced by at least one of the dialysate flow, blood flow, and infusate flow) varies from a positive 300 mmHg, or more, to a negative 100 mmHg, or less, over a period of time of less than 0.5 seconds anywhere along the fluidic circuit of the dialysate, blood, or infusate flow and particularly within the manifold.

22. The pressure amplitude (experienced by at least one of the dialysate flow, blood flow, and infusate flow) varies from a positive 300 mmHg, or more, to a negative 100 mmHg, or less, over a period of time of less than 0.25 seconds anywhere along the fluidic circuit of the dialysate, blood, or infusate flow and particularly within the manifold.

23. The pressure amplitude (experienced by at least one of the dialysate flow, blood flow, and infusate flow) varies from a positive 300 mmHg, or more, to a negative 100 mmHg, or less, over a period of time of less than 0.15 seconds anywhere along the fluidic circuit of the dialysate, blood, or infusate flow and particularly within the manifold.

24. The pressure amplitude (experienced by at least one of the dialysate flow, blood flow, and infusate flow) varies from a positive 300 mmHg, or more, to a negative 100 mmHg, or less, over a period of time of less than 0.1 seconds anywhere along the fluidic circuit of the dialysate, blood, or infusate flow and particularly within the manifold.

25. The pressure amplitude (experienced by at least one of the dialysate flow, blood flow, and infusate flow) varies from a positive 300 mmHg, or more, to a negative 100 mmHg, or less, over a period of time of less than 0.05 seconds anywhere along the fluidic circuit of the dialysate, blood, or infusate flow and particularly within the manifold.

26. The pressure amplitude experienced by at least one of the dialysate flow, blood flow, and infusate flow changes from positive pressure to negative pressure in less than 1 second, preferably less than 0.5 seconds, preferably less than 0.25 seconds, preferably less than 0.15 seconds, preferably less than 0.1 seconds, and preferably less than 0.05 seconds and the magnitude of this pressure amplitude change increases as the flow rate increases for the corresponding dialysate flow, blood flow, and infusate flow anywhere along the fluidic circuit of the dialysate, blood, or infusate flow and particularly within the manifold.

27. The pressure amplitude experienced by at least one of the dialysate flow, blood flow, and infusate flow changes from positive pressure to negative pressure in less than 1 second, preferably less than 0.5 seconds, preferably less than 0.25 seconds, preferably less than 0.15 seconds, preferably less than 0.1 seconds, and preferably less than 0.05 seconds and the magnitude of this pressure amplitude change decreases as the flow rate decreases for the corresponding dialysate flow, blood flow, and infusate flow anywhere along the fluidic circuit of the dialysate, blood, or infusate flow and particularly within the manifold.

28. The pressure amplitude experienced by at least one of the dialysate flow, blood flow, and infusate flow cycles between a positive pressure and a negative pressure at least once in less than 1 second, preferably less than 0.5 seconds, preferably less than 0.25 seconds, preferably less than 0.15 seconds, preferably less than 0.1 seconds, and preferably less than 0.05 seconds.

29. The pressure amplitude experienced by at least one of the dialysate flow, blood flow, and infusate flow cycles between a positive pressure and a negative pressure at least twice in less than 1 second, preferably less than 0.5 seconds, preferably less than 0.25 seconds, preferably less than 0.15 seconds, preferably less than 0.1 seconds, and preferably less than 0.05 seconds.

30. The pressure amplitude experienced by at least one of the dialysate flow, blood flow, and infusate flow cycles between a positive pressure and a negative pressure at least three times in less than 1 second, preferably less than 0.5 seconds, preferably less than 0.25 seconds, preferably less than 0.15 seconds, preferably less than 0.1 seconds, and preferably less than 0.05 seconds.

Figures 8A, 8B:
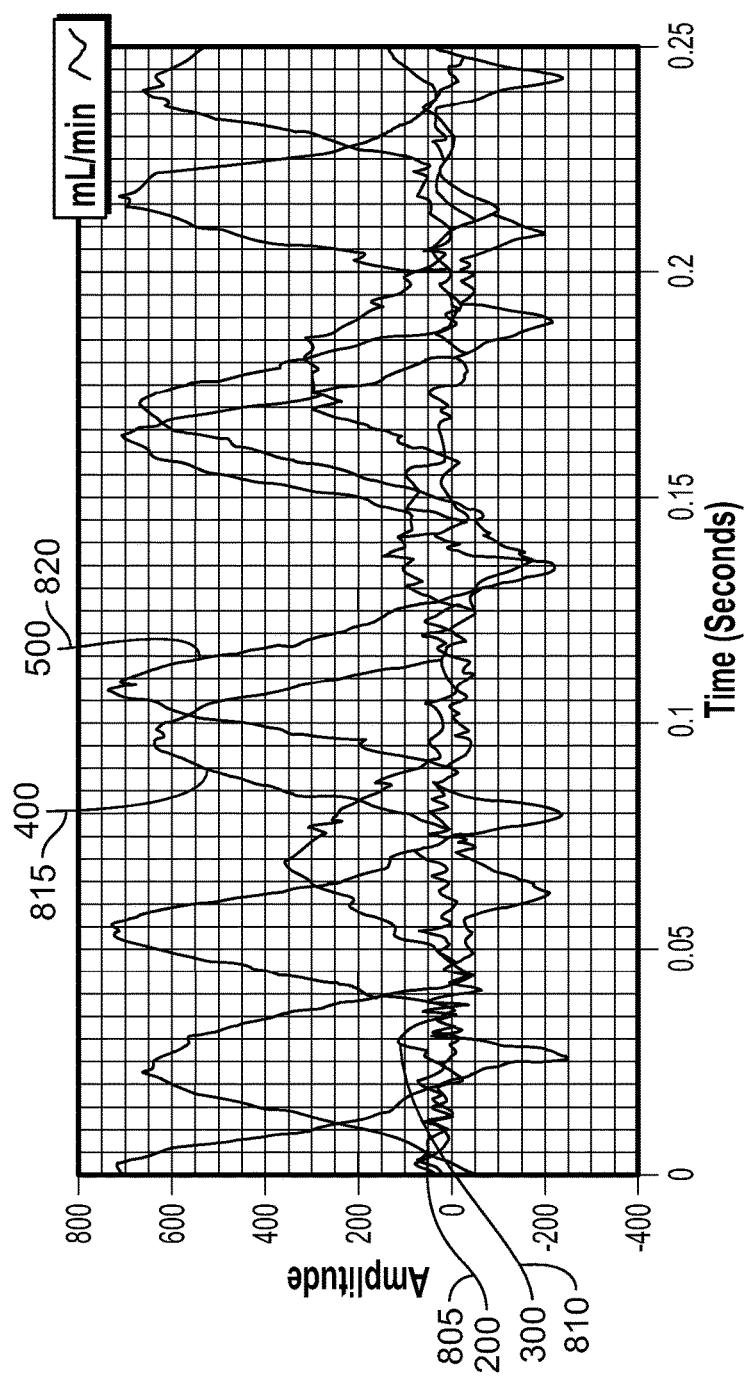
FIG. 8*a* is a graph illustrating exemplary pressure waveforms generated at specific flow rates within a blood circuit of a dialysis system, in accordance with various aspects of the present specification.
FIG. 8*b* is a table illustrating the pressure amplitude range and the average pressure for various flow rates, in accordance with an aspect of the present specification.

FIG. 8a is a graph illustrating exemplary pressure waveforms generated at specific flow rates within a blood circuit of a dialysis system, in accordance with various aspects of the present specification. Specifically, FIG. 8 shows instantaneous or real time pressure profiles 805, 810, 815 and 820 generated by the blood circuit at respective flow rates of 200 mL/min, 300 mL/min, 400 mL/min and 500 mL/min. It may be noted that while the instantaneous or real time pressure profiles 805, 810, 815, 820 are defined by cycles of high or positive and low or negative pressures, the corresponding mean or average pressure profiles are positive. Also, as the flow rate increases from 200 mL/min to 500 ml/min the instantaneous or real time pressure profiles 805, 810, 815, 820 are characterized by waves of increasing amplitude range.

FIG. 8b is a table illustrating the pressure amplitude range and the average pressure for various flow rates. Referring to FIG. 8b, in an exemplary embodiment, for a flow rate of 200 ml/min 850, the minimum and maximum pressure amplitude range from −50 mmHg to 160 mmHg, when the pump is run over a period of 26 milliseconds. The average or mean pressure at this flow rate is 26 mmHg. For a flow rate of 300 ml/min 860, the minimum and maximum pressure amplitude range from −70 mmHg to 375 mmHg, when the pump is operated over a period of 30 milliseconds. The average or mean pressure at this flow rate is 102 mmHg. Similarly, for a flow rate of 400 ml/min 870, the minimum and maximum pressure amplitude range from −220 mmHg to 650 mmHg, when the pump is operated over a period of 35 milliseconds. The average or mean pressure at this flow rate is 175 mmHg. For a flow rate of 500 ml/min 880, the minimum and maximum pressure amplitude range from −275 mmHg to 750 mmHg, when the pump is run over a period of 30 milliseconds. The average or mean pressure at this flow rate is 245 mmHg. Note that, in each case, the pressure changes from positive to negative and back in less than 1 second, preferably less than 0.5 seconds, preferably less than 0.25 second, preferably less than 0.15 seconds, preferably less than 0.1 seconds, and more preferably less than 0.05 seconds.

Referring now to FIGS. 2, 8a and 8b, during operation, at time 0, the dialysis system 200 is switched on, and the blood pump begins rotating, applying a force to the pump tube segment 201 and causing blood to flow through port C 217, through port A 215, and into the dialyzer 230. Concurrently, the fresh dialysate pumps begin rotating, applying a force to the pump tube segment 203 and causing dialysate to flow through port E 219, through port H 222, and into the dialyzer 230. In some embodiments, the blood pump has a diameter rotor size of 4 inches or less and 4 to 6 rollers equidistantly distributed around its circumference. Taking an exemplary case of the flow rate of 500 ml/min, when the fresh dialysate pump begins operating, it takes approximately 30 milliseconds to reach a flow rate of 500 ml/min. When the blood flow reaches a steady state having a flow rate of 500 ml/min, the instantaneous pressure profile of the blood flow ranges from an amplitude of −275 mmHg to 750 mmHg over a period of 30 milliseconds. This is caused because, at a first point in time, blood is filling the tube segment 201, at which point the instantaneous pressure profile reaches a maximum amplitude of around 750 mm Hg. At a second point in time, approximately 30 milliseconds after the first point in time, the blood is expelled from the tube segment 201, at which point the instantaneous pressure profile reaches a minimum amplitude of about −275 mmHg. In one implementation, when the fresh dialysate pump begins operating, it takes approximately 3 to 5 seconds to reach a flow rate specified or pre-determined by a user. This can be in the range of 300 mL/min to 500 mL/min and is defined in increments of 50 mL/min.

Figure 9:
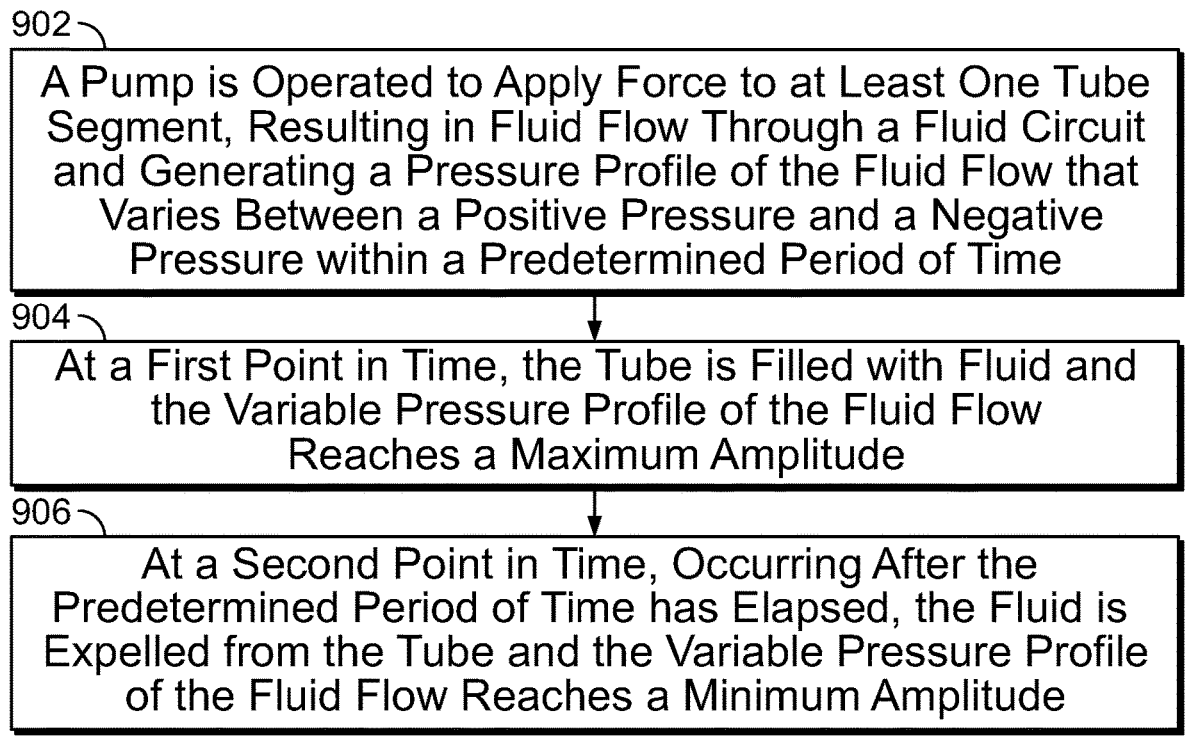
FIG. 9 is a flow chart listing the steps involved in operating a pump of a portable dialysis system to generate a variable pressure profile in a tube segment of said system, in accordance with some embodiments of the present specification.

FIG. 9 is a flow chart listing the steps involved in operating a pump of a portable dialysis system to generate a variable pressure profile in a tube segment of said system, in accordance with some embodiments of the present specification. At step 902, at least one pump of the portable dialysis system is operated to apply force to at least one tube segment, resulting in fluid flow through a fluid circuit and generating a pressure profile of said fluid flow that varies between a positive pressure and a negative pressure within a predetermined amount of time. The fluid circuit is any one of a dialysate circuit and blood circuit in fluid communication with the tube segment. In various embodiments, the point at which the pressure is measured is within a disposable manifold of the portable dialysis system. At step 904, at a first point in time, the tube is filled with fluid, and the variable pressure profile of the fluid flow reaches a maximum amplitude. At step 906, at a second point in time, occurring after the predetermined period has elapsed, the fluid is expelled from the tube, and the variable pressure profile of the fluid flow reaches a minimum amplitude.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for providing increasing clearance levels of blood toxins comprising:
    providing a portable dialysis system comprising:
        a manifold, comprising a plurality of blood and dialysate circuits;
        at least one tube segment in fluid communication with at least one of the blood and dialysate circuits;
        a pump for pumping a fluid through the at least one tube segment and at least one of the plurality of blood and dialysate circuits; and
    operating the pump to apply a force to the at least one tube segment to generate fluid flow through the at least one tube segment, wherein the pump is configured to generate the fluid flow with a pressure profile that varies between a positive pressure and a negative pressure within a predetermined period and wherein the fluid flow continues flowing in a same direction while the pressure profile varies between the positive pressure and the negative pressure.

2. The method of claim 1, wherein the pump comprises a rotor pump having a plurality of rollers.

3. The method of claim 2, wherein the rotor pump has a diameter no greater than 4 inches.

4. The method of claim 2, wherein the rotor pump has a range of 4 to 6 rollers.

5. The method of claim 2, wherein each of the plurality of rollers comprises a plurality of equidistantly spaced cylindrical pins.

6. The method of claim 5, wherein the plurality of equidistantly spaced cylindrical pins is in a range of 4 to 6.

7. The method of claim 1, wherein the fluid flow is any one of dialysate flow, blood flow, and infusate flow.

8. The method of claim 1, wherein a change in pressure amplitude experienced by the fluid flow is at least 100 mmHg and the predetermined period is less than 0.5 seconds.

9. The method of claim 1, wherein a change in pressure amplitude experienced by the fluid flow is at least 100 mmHg and the predetermined period is less than 0.05 seconds.

10. The method of claim 1, wherein a change in pressure amplitude experienced by the fluid flow is at least 200 mmHg and the predetermined period is less than 0.5 seconds.

11. The method of claim 1, wherein a change in pressure amplitude experienced by the fluid flow is at least 200 mmHg and the predetermined period is less than 0.05 seconds.

12. The method of claim 1, wherein an amplitude of the pressure profile varies from a positive 100 mmHg, or more, to a negative 25 mmHg, or less, over a period less than 0.5 seconds.

13. The method of claim 1, wherein an amplitude of the pressure profile varies from a positive 100 mmHg, or more, to a negative 25 mmHg, or less, over a period less than 0.05 seconds.

14. The method of claim 1, wherein an amplitude of the pressure profile varies from a positive 200 mmHg, or more, to a negative 50 mmHg, or less, over a period less than 0.5 seconds.

15. The method of claim 1, wherein an amplitude of the pressure profile varies from a positive 300 mmHg, or more, to a negative 100 mmHg, or less, over a period of less than 0.5 seconds.

16. The method of claim 1, wherein a pressure amplitude of the fluid flow changes from positive pressure to negative pressure in less than 1 second and wherein a magnitude of the pressure amplitude change increases as the flow rate increases for the corresponding fluid flow.

17. The method of claim 1, wherein a pressure amplitude of the fluid flow changes from positive pressure to negative pressure in less than 1 second and a magnitude of the pressure amplitude change decreases as the flow rate decreases for the corresponding fluid flow.

18. The method of claim 1, wherein a pressure amplitude of the fluid flow cycles between a positive pressure and a negative pressure at least once in less than 0.5 seconds.

19. The method of claim 1, wherein a pressure amplitude of the fluid flow cycles between a positive pressure and a negative pressure at least twice in less than 0.5 seconds.

20. The method of claim 1, wherein a pressure amplitude of the fluid flow cycles between a positive pressure and a negative pressure at least three times in less than 0.5 seconds.

21. The method of claim 1, further comprising operating the pump to fill the tube segment with the fluid at a first point in time such that the pressure profile reaches a maximum amplitude and operating the pump to expel the fluid from the tube at a second point in time, occurring after the predetermined period, such that the pressure profile reaches a minimum amplitude.

22. A method for providing increasing clearance levels of blood toxins comprising:
providing a portable dialysis system comprising:
a manifold comprising a blood circuit, wherein the blood circuit has at least one tube segment;
a rotor pump for pumping a blood through the at least one tube segment, wherein the rotor pump has a diameter no greater than 4 inches; and
operating the rotor pump to apply a force to the at least one tube segment to generate blood flow through the at least one tube segment, wherein the rotor pump is configured to generate the blood flow with a pressure profile that varies between a positive pressure and a negative pressure within a predetermined period, wherein an amplitude of the pressure profile varies from a positive 100 mmHg, or more, to a negative 25 mmHg, or less, over a period less than 0.5 seconds and wherein an average pressure of the blood flow remains positive over a period of at least 5 seconds; and wherein the fluid flow continues flowing in a same direction while the pressure profile varies between the positive pressure and the negative pressure.

23. A dialysis system for providing increasing clearance levels of blood toxins comprising:
a manifold comprising a blood circuit, wherein the blood circuit has at least one tube segment;
a rotor pump in physical communication with the at least one tube segment and configured to pump blood through the at least one tube segment, wherein the rotor pump has a diameter no greater than 4 inches; and
a controller configured to operate the rotor pump to apply a force to the at least one tube segment to generate blood flow through the at least one tube segment, wherein the controller is adapted to control the rotor pump to generate the blood flow with a pressure profile that varies between a positive pressure and a negative pressure within a predetermined period, wherein the fluid flow continues flowing in a same direction while the pressure profile varies between the positive pressure and the negative pressure.

24. The dialysis system of claim 23 further comprising a single fluid reservoir having a fluid capacity no greater than 10 liters.

25. The dialysis system of claim 23 wherein the rotor pump has a range of 4 to 6 rollers.

26. The dialysis system of claim 23 wherein the blood toxins include compositions having a molecular weight greater than 500 Daltons.

27. The dialysis system of claim 23, wherein a change in pressure amplitude experienced by the blood flow is at least 100 mmHg and the predetermined period is less than 0.5 seconds.

28. The dialysis system of claim 23, wherein a change in pressure amplitude experienced by the blood flow is at least 100 mmHg and the predetermined period is less than 0.05 seconds.

29. The dialysis system of claim 23, wherein a change in pressure amplitude experienced by the blood flow is at least 200 mmHg and the predetermined period is less than 0.5 seconds.

30. The dialysis system of claim 23, wherein a change in pressure amplitude experienced by the blood flow is at least 200 mmHg and the predetermined period is less than 0.05 seconds.

31. The dialysis system of claim 23, wherein an amplitude of the pressure profile varies from a positive 100 mmHg, or more, to a negative 25 mmHg, or less, over a period less than 0.5 seconds.

32. The dialysis system of claim 23, wherein an amplitude of the pressure profile varies from a positive 100 mmHg, or more, to a negative 25 mmHg, or less, over a period less than 0.05 seconds.

33. The dialysis system of claim 23, wherein an amplitude of the pressure profile varies from a positive 200 mmHg, or more, to a negative 50 mmHg, or less, over a period less than 0.5 seconds.

34. The dialysis system of claim 23, wherein an amplitude of the pressure profile varies from a positive 300 mmHg, or more, to a negative 100 mmHg, or less, over a period of less than 0.5 seconds.

35. The dialysis system of claim 23, wherein a pressure amplitude of the blood flow changes from positive pressure to negative pressure in less than 1 second and wherein a magnitude of the pressure amplitude change increases as the blood flow rate increases for the corresponding blood flow.

36. The dialysis system of claim 23, wherein a pressure amplitude of the blood flow changes from positive pressure to negative pressure in less than 1 second and a magnitude of the pressure amplitude change decreases as the blood flow rate decreases for the corresponding blood flow.

37. The dialysis system of claim 23, wherein a pressure amplitude of the blood flow cycles between a positive pressure and a negative pressure at least once in less than 0.5 seconds.

38. The dialysis system of claim 23, wherein a pressure amplitude of the blood flow cycles between a positive pressure and a negative pressure at least twice in less than 0.5 seconds.

39. The dialysis system of claim 23, wherein a pressure amplitude of the blood flow cycles between a positive pressure and a negative pressure at least three times in less than 0.5 seconds.

40. The dialysis system of claim 23, wherein an amplitude of the pressure profile varies from a positive 100 mmHg, or more, to a negative 25 mmHg, or less, over a period less than 0.5 seconds and wherein an average pressure of the blood flow remains positive over a period of at least 5 seconds.

* * * * *